US009822169B2

(12) United States Patent
Hellstrom et al.

(10) Patent No.: US 9,822,169 B2
(45) Date of Patent: Nov. 21, 2017

(54) COMPOSITIONS AND METHODS OF USE FOR DETERMINATION OF HE4A

(75) Inventors: Ingegerd Hellstrom, Seattle, WA (US); Karl-Erik Hellstrom, Seattle, WA (US); John Raycraft, Clayton, CA (US); Christian Fermér, Västra Frölunda (SE); Eva Roijer, Västra Frölunda (SE)

(73) Assignees: PACIFIC NORTHWEST DIABETES RESEARCH INSTITUTE, Seattle, WA (US); FUJIREBIO DIAGNOSTICS, INC., Malvern, PA (US)

( * ) Notice: Subject to any disclaimer, the term of this patent is extended or adjusted under 35 U.S.C. 154(b) by 437 days.

(21) Appl. No.: 13/985,983

(22) PCT Filed: Feb. 17, 2011

(86) PCT No.: PCT/US2011/025321
§ 371 (c)(1),
(2), (4) Date: Dec. 16, 2013

(87) PCT Pub. No.: WO2012/112160
PCT Pub. Date: Aug. 23, 2012

(65) Prior Publication Data
US 2015/0353629 A1 Dec. 10, 2015

(51) Int. Cl.
| *C07K 16/38* | (2006.01) |
| *C07K 16/18* | (2006.01) |
| *C07K 16/46* | (2006.01) |
| *C07K 16/30* | (2006.01) |
| *G01N 33/574* | (2006.01) |
| *C07K 14/81* | (2006.01) |

(52) U.S. Cl.
CPC .......... *C07K 16/18* (2013.01); *C07K 16/3069* (2013.01); *G01N 33/57411* (2013.01); *G01N 33/57449* (2013.01); *C07K 2317/14* (2013.01); *G01N 2800/52* (2013.01)

(58) Field of Classification Search
CPC ........ C07K 16/18; C07K 16/30; C07K 16/38; C07K 16/461; C07K 16/462; C07K 16/464; C07K 16/468; C07K 2317/14; C07K 14/81
See application file for complete search history.

(56) References Cited

U.S. PATENT DOCUMENTS

| 7,270,960 | B2 * | 9/2007 | Hellstrom | C07K 14/811 435/7.1 |
| 2003/0108965 | A1 | 6/2003 | Schummer et al. | |
| 2008/0020473 | A1 | 1/2008 | Moore et al. | |
| 2009/0075307 | A1 | 3/2009 | Fischer et al. | |

FOREIGN PATENT DOCUMENTS

| WO | 2006/089125 | 8/2006 |
| WO | 2008/112514 | 9/2008 |
| WO | 2012/027631 | 3/2012 |

OTHER PUBLICATIONS

Hellstrom, I., et al., Cancer Research, 63: 3695-3700, 2003.*
Drapkin, R., et al, Cancer Research, 65(6): 2162-2169, 2005.*
OriGene Technologies Inc., pp. 1-2, Polyclonal Antibody to WFDC2/WAP5 (29-43), Catalog No. AP22455PU-N; downloaded Apr. 2016.*
Pettersen et al., J. Immunol. Jun. 15, 1999; 162 (12): 7031-7040.*
Bernard et al., Human Immunol. 1986; 17: 388-405.*
International Search Report in PCT/US2012/028451 for PCT/US2011/025321, dated Aug. 23, 2012.
Written Opinion of the International Search Authority for PCT/US2011/025321, dated Aug. 17, 2013.
(IB/373) International Preliminary Report on Patentability Chapter I PCT/US2011/025321, dated Aug. 21, 2013.
Everest biotech: "Data Sheet EB09963—Goat Anti-WFDC2 (aa29-43) Antibody".
Genome Cube: "Data Sheet Product Goat anti-WFDC2 (aa29-43) Antibody".
EP Search Report dated Mar. 3, 2015 for corresponding EP Application No. 11858800.3.
Li, Jinping et al., "HE4 as a biomarker for ovarian and endometrial cancer management", Expert Rev. Mol. Diagn. Sep. 2009; 9(6): 555-566.
GenBank: AF330262.1 "*Homo sapiens* WAP domain containing protein HE4-V4 (WFDC2) mRNA, complete cds, alternatively spliced".
GenBank: AAL37486.1 "WAP domain containing protein HE4-V2 [*Homo sapiens*]".
Rudikoff, Stuart et al., "Single amino acid substitution altering antigen-binding specificity" Proc. Nat. Acad. Sci. USA, vol. 79, No. 6, pp. 1979-1983, Mar. 1982.
Tamura, Midori et al., "Structural Correlates of an Anticarcinoma Antibody: Identification of Specificity-Determining Residues (SDRs) and Development of a Minimally Immunogenic Antibody Variant by Retention of SDRs Only" The Journal of Immunology, vol. 164, Issue 3, pp. 1432-1441, Feb. 2000.
Office Action dated Dec. 19, 2016 for corresponding Canadian Patent Application No. 2,827,618.

(Continued)

*Primary Examiner* — Jeffrey Stucker
*Assistant Examiner* — Anne Holleran
(74) *Attorney, Agent, or Firm* — Duane Morris LLP

(57) ABSTRACT

The invention includes the use of the HE/HE4a markers to assess ovarian cancer in a subject. Included also are compositions and methods of using HE/HE4a marker for diagnosis, grading and staging of ovarian cancers, determining prognosis and treatment effectiveness of a subject who has been diagnosed with ovarian cancer.

6 Claims, 12 Drawing Sheets

(56) References Cited

OTHER PUBLICATIONS

Altshuler, E. P. et al., "Generation of Recombinant Antibodies and Means for Increasing Their Affinity" Biochemistry (Moscow), 2010, vol. 75, No. 13, pp. 1584-1605 (Original Russian Text published in Uspekhi Biologicheskoi Khimii, 2010, vol. 50, pp. 203-258).

Office Action dated May 25, 2016 for corresponding Russian Patent Application No. 2013142334.

\* cited by examiner

```
                            M  P  A  C  R  L  G  P
  2 gagagaaagcggccgcaccgccggcatagcaccatgcctgcttgtcgcctaggccg   61  Bold = Leader
    L  A  A  A  L  L  S  L  L  L  F  Q  P  T  L  V  S  G  T           seq
 62 ctagccgccgcctcctcctcagcctgctgctgttcggcttcaccctagtctcaggcaca 121
    Q  A  E  K  T  G  V  C  P  E  L  Q  A  D  Q  N  C  T  Q  E
122 ggagcagagaagactggcgtgtgccccgagctccaggctgaccagaactgcacgcaagag 181  Black = N-WFDC
    C  V  S  D  S  K  C  A  D  N  L  K  C  C  S  A  G  C  A  T
182 tgcgtctcggacagcaatgcgccgacaacctcaagtgctgcagcgcgggtgtgccacc    241
    F  C  S  L  P  N  D  K  E  G  S  C  P  Q  V  N  I  N  F  P
242 ttctgtctctgcccaatgataaggagggttcctgccccagtgaacattaactttccc    301
    Q  L  G  L  C  E  D  Q  C  Q  P  D  Q  Q  C  E  G  Q  K  K
302 cagctcggcctctgtcgggaccagtgccaggtggacagccagtgtcctggccagatgaaa 361  Italics = C-WFDC
    C  C  R  N  G  C  Q  K  V  S  C  V  P  K  K  *
362 tgctgccgcaatggctgtgggaaggtgtcctgtgtcactcccaattctgagctcgggcc   421

422 accaccaggctgagcagtgaagatagaaagtttctgctggccctgcagcgtgttacagc   481

482 ccacc                                   486
```

Figure 4

SEQUENCE LISTING

```
<160> NUMBER OF SEQ ID NOS: 39

<210> SEQ ID NO 1
<211> LENGTH: 124
<212> TYPE: PRT
<213> ORGANISM: Homo sapiens
<220> FEATURE:
<223> OTHER INFORMATION: WAP four-disulfide core domain protein 2
      precursor

<400> SEQUENCE: 1

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
        115                 120

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttgttaagc ttgccgccat gcctgcttgt cgcctaggc                         39

<210> SEQ ID NO 3
<211> LENGTH: 102
<212> TYPE: PRT
<213> ORGANISM: Homo sapiens
<220> FEATURE:
<223> OTHER INFORMATION: WAP domain containing protein HE4-V4

<400> SEQUENCE: 3

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
```

```
                    35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Ala Leu Phe His Trp His
65                  70                  75                  80

Leu Lys Thr Arg Arg Leu Trp Glu Ile Ser Gly Pro Arg Pro Arg Arg
                85                  90                  95

Pro Thr Trp Asp Ser Ser
            100

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttgttggat ccgaaattgg gagtgacaca ggacac                             36

<210> SEQ ID NO 5
<211> LENGTH: 73
<212> TYPE: PRT
<213> ORGANISM: Homo sapiens
<220> FEATURE:
<223> OTHER INFORMATION: WAP domain containing protein HE4-V3

<400> SEQUENCE: 5

Met Leu Gln Val Gln Val Asn Leu Pro Val Ser Pro Leu Pro Thr Tyr
1               5                   10                  15

Pro Tyr Ser Phe Phe Tyr Pro Asp Lys Glu Gly Ser Cys Pro Gln Val
            20                  25                  30

Asn Ile Asn Phe Pro Gln Leu Gly Leu Cys Arg Asp Gln Cys Gln Val
        35                  40                  45

Asp Ser Gln Cys Pro Gly Gln Met Lys Cys Cys Arg Asn Gly Cys Gly
    50                  55                  60

Lys Val Ser Cys Val Thr Pro Asn Phe
65                  70

<210> SEQ ID NO 6
<211> LENGTH: 485
<212> TYPE: DNA
<213> ORGANISM: Homo sapiens
<220> FEATURE:
<221> NAME/KEY: CDS
<222> LOCATION: (37)..(408)

<400> SEQUENCE: 6
gagagaaagc ggccgcaccc cgcccggcat agcacc atg cct gct tgt cgc cta      54
                                       Met Pro Ala Cys Arg Leu
                                       1               5 ggc ccg cta gcc gcc gcc ctc ctc ctc agc ctg ctg ctg ttc ggc ttc     102
Gly Pro Leu Ala Ala Ala Leu Leu Leu Ser Leu Leu Leu Phe Gly Phe
            10                  15                  20 acc cta gtc tca ggc aca gga gca gag aag act ggc gtg tgc ccc gag     150
Thr Leu Val Ser Gly Thr Gly Ala Glu Lys Thr Gly Val Cys Pro Glu
        25                  30                  35 ctc cag gct gac cag aac tgc acg caa gag tgc gtc tcg gac agc gaa     198
Leu Gln Ala Asp Gln Asn Cys Thr Gln Glu Cys Val Ser Asp Ser Glu
    40                  45                  50
```

```
tgc gcc gac aac ctc aag tgc tgc agc gcg ggc tgt gcc acc ttc tgc      246
Cys Ala Asp Asn Leu Lys Cys Cys Ser Ala Gly Cys Ala Thr Phe Cys
 55              60                  65                  70 tct ctg ccc aat gat aag gag ggt tcc tgc ccc cag gtg aac att aac      294
Ser Leu Pro Asn Asp Lys Glu Gly Ser Cys Pro Gln Val Asn Ile Asn
             75                  80                  85 ttt ccc cag ctc ggc ctc tgt cgg gac cag tgc cag gtg gac agc cag      342
Phe Pro Gln Leu Gly Leu Cys Arg Asp Gln Cys Gln Val Asp Ser Gln
         90                  95                 100 tgt cct ggc cag atg aaa tgc tgc cgc aat ggc tgt ggg aag gtg tcc      390
Cys Pro Gly Gln Met Lys Cys Cys Arg Asn Gly Cys Gly Lys Val Ser
    105                 110                 115 tgt gtc act ccc aat ttc tgagctccgg ccaccaccag gctgagcagt             438
Cys Val Thr Pro Asn Phe
            120 gaagatagaa agtttctgcc tggccctgca gcgtgttaca gcccacc                  485

<210> SEQ ID NO 7
<211> LENGTH: 76
<212> TYPE: PRT
<213> ORGANISM: Homo sapiens
<220> FEATURE:
<223> OTHER INFORMATION: WAP domain containing protein HE4-V2

<400> SEQUENCE: 7

Met Pro Ala Cys Arg Leu Gly Pro Leu Ala Ala Leu Leu Leu Leu Ser
 1               5                  10                  15

Leu Leu Leu Phe Gly Phe Thr Leu Val Ser Asp Lys Glu Gly Ser Cys
             20                  25                  30

Pro Gln Val Asn Ile Asn Phe Pro Gln Leu Gly Leu Cys Arg Asp Gln
         35                  40                  45

Cys Gln Val Asp Ser Gln Cys Pro Gly Gln Met Lys Cys Cys Arg Asn
    50                  55                  60

Gly Cys Gly Lys Val Ser Cys Val Thr Pro Asn Phe
 65                  70                  75

<210> SEQ ID NO 8

<400> SEQUENCE: 8

000

<210> SEQ ID NO 9
<211> LENGTH: 80
<212> TYPE: PRT
<213> ORGANISM: Homo sapiens
<220> FEATURE:
<223> OTHER INFORMATION: WAP domain containing protein HE4-V1

<400> SEQUENCE: 9

Met Pro Ala Cys Arg Leu Gly Pro Leu Ala Ala Leu Leu Leu Leu Ser
 1               5                  10                  15

Leu Leu Leu Phe Gly Phe Thr Leu Val Ser Gly Thr Gly Ala Glu Lys
             20                  25                  30

Thr Gly Val Cys Pro Glu Leu Gln Ala Asp Gln Asn Cys Thr Gln Glu
         35                  40                  45

Cys Val Ser Asp Ser Glu Cys Ala Asp Asn Leu Lys Cys Cys Ser Ala
    50                  55                  60

Gly Cys Ala Thr Phe Cys Leu Leu Cys Pro Asn Gly Gln Leu Ala Glu
 65                  70                  75                  80
```

<210> SEQ ID NO 10

<400> SEQUENCE: 10

000

<210> SEQ ID NO 11
<211> LENGTH: 124
<212> TYPE: PRT
<213> ORGANISM: Homo sapiens
<220> FEATURE:
<223> OTHER INFORMATION: WAP four-disulfide core domain 2

<400> SEQUENCE: 11

```
Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110

Gly Cys Gly Lys Val Ser Cys Val Thr Pro Asn Phe
        115                 120
```

<210> SEQ ID NO 12

<400> SEQUENCE: 12

000

<210> SEQ ID NO 13
<211> LENGTH: 124
<212> TYPE: PRT
<213> ORGANISM: Homo sapiens
<220> FEATURE:
<223> OTHER INFORMATION: HE4 protein

<400> SEQUENCE: 13

```
Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
                85                  90                  95

Cys Gln Val Asp Ser Gln Cys Pro Gly Gln Met Lys Cys Cys Arg Asn
            100                 105                 110
```

Gly Cys Gly Lys Val Ser Cys Val Thr Pro Asn Phe
        115                 120

<210> SEQ ID NO 14

<400> SEQUENCE: 14

000

<210> SEQ ID NO 15
<211> LENGTH: 125
<212> TYPE: PRT
<213> ORGANISM: Homo sapiens
<220> FEATURE:
<223> OTHER INFORMATION: HE4 protein

<400> SEQUENCE: 15

Met Pro Ala Cys Arg Leu Gly Pro Leu Ala Ala Leu Leu Leu Leu Ser
1               5                   10                  15

Leu Leu Leu Phe Gly Phe Thr Leu Val Ser Gly Thr Gly Ala Glu Lys
            20                  25                  30

Thr Gly Val Cys Pro Glu Leu Gln Ala Asp Gln Asn Cys Thr Gln Glu
        35                  40                  45

Cys Val Ser Asp Ser Glu Cys Ala Asp Asn Leu Lys Cys Cys Ser Ala
    50                  55                  60

Gly Cys Ala Thr Phe Cys Leu Leu Cys Pro Asn Asp Lys Glu Gly Ser
65                  70                  75                  80

Cys Pro Gln Val Asn Ile Asn Phe Pro Gln Leu Gly Leu Cys Arg Asp
                85                  90                  95

Gln Cys Gln Val Asp Thr Gln Cys Pro Gly Gln Met Lys Cys Cys Arg
            100                 105                 110

Asn Gly Cys Gly Lys Val Ser Cys Val Thr Pro Asn Phe
        115                 120                 125

<210> SEQ ID NO 16

<400> SEQUENCE: 16

000

<210> SEQ ID NO 17
<211> LENGTH: 45
<212> TYPE: PRT
<213> ORGANISM: Homo sapiens
<220> FEATURE:
<223> OTHER INFORMATION: HE4a N-WFDC

<400> SEQUENCE: 17

Glu Lys Thr Gly Val Cys Pro Glu Leu Gln Ala Asp Gln Asn Cys Thr
1               5                   10                  15

Gln Glu Cys Val Ser Asp Ser Glu Cys Ala Asp Asn Leu Lys Cys Cys
            20                  25                  30

Ser Ala Gly Cys Ala Thr Phe Cys Ser Leu Pro Asn Asp
        35                  40                  45

<210> SEQ ID NO 18

<400> SEQUENCE: 18

000

<210> SEQ ID NO 19

```
<211> LENGTH: 49
<212> TYPE: PRT
<213> ORGANISM: Homo sapiens
<220> FEATURE:
<223> OTHER INFORMATION: HE4a C-WFDC

<400> SEQUENCE: 19

Lys Glu Gly Ser Cys Pro Gln Val Asn Ile Asn Phe Pro Gln Leu Gly
  1               5                  10                  15

Leu Cys Arg Asp Gln Cys Gln Val Asp Ser Gln Cys Pro Gly Gln Met
             20                  25                  30

Lys Cys Cys Arg Asn Gly Cys Gly Lys Val Ser Cys Val Thr Pro Asn
         35                  40                  45

Phe

<210> SEQ ID NO 20

<400> SEQUENCE: 20

000

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      HE4a-V4: Forward primer

<400> SEQUENCE: 21
gttgttaccg gtgcagcaga gaagactggc gtgtgcccc                              39

<210> SEQ ID NO 22

<400> SEQUENCE: 22

000

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      HE4a-V4 Reverse primer

<400> SEQUENCE: 23
aatctcccag agcctccgtg tctttaggtg ccagtggaac agtgcattgg gcagagagca      60

<210> SEQ ID NO 24

<400> SEQUENCE: 24

000

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      HE4a-V2: Forward primer

<400> SEQUENCE: 25
gttgttaccg gtgcaaagga gggttcctgc ccccag                                36
```

<210> SEQ ID NO 26

<400> SEQUENCE: 26

000

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      HE4a-V2: Reverse primer

<400> SEQUENCE: 27
gttgttggat ccgaaattgg gagtgacaca gga                           33

<210> SEQ ID NO 28

<400> SEQUENCE: 28

000

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      PCR primer used to generate N-WFDC domain

<400> SEQUENCE: 29
tgctaagctt tgccgagaag actggcgtgt gccc                          34

<210> SEQ ID NO 30

<400> SEQUENCE: 30

000

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer used to generate N-WFDC domain

<400> SEQUENCE: 31
ccttctgcag gatcattggg cagagagcag                               30

<210> SEQ ID NO 32

<400> SEQUENCE: 32

000

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      PCR primer used to generate C-WFDC domain

<400> SEQUENCE: 33
tgctaagctt tgccaaggag ggttcctgcc ccca                          34

<210> SEQ ID NO 34

<400> SEQUENCE: 34

000

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      PCR primer used to generate C-WFDC domain

<400> SEQUENCE: 35
ccttctgcag ggaaattggg agtgacacag ga                                    32

<210> SEQ ID NO 36

<400> SEQUENCE: 36

000

<210> SEQ ID NO 37
<211> LENGTH: 583
<212> TYPE: DNA
<213> ORGANISM: Homo sapiens
<220> FEATURE:
<223> OTHER INFORMATION: HE4 mRNA for extracellular proteinase inhibitor
      homologue

<400> SEQUENCE: 37
cccctgcacc cgcccggca tagcaccatg cctgcttgtc gcctaggccc gctagccgcc        60
gccctcctcc tcagcctgct gctgttcggc ttcaccctag tctcaggcac aggagcagag      120
aagactggcg tgtgccccga gctccaggct gaccagaact gcacgcaaga gtgcgtctcg      180
gacagcgaat gcgccgacaa cctcaagtgc tgcagcgcgg gctgtgccac cttctgcctt      240
ctctgcccca atgataagga gggttcctgc ccccaggtga acattaactt tccccagctc      300
ggcctctgtc gggaccagtg ccaggtggac acgcagtgtc ctggccagat gaaatgctgc      360
cgcaatggct gtgggaaggt gtcctgtgtc actcccaatt tctgaggtcc agccaccacc      420
aggctgagca gtgaggagag aaagtttctg cctggccctg catctggttc cagcccacct      480
gccctcccct ttttcgggac tctgtattcc ctcttggggt gaccacagct tctcccttttc    540 ccaaccaata aagtaaccac tttcagcaaa aaaaaaaaaa aaa                        583

<210> SEQ ID NO 38

<400> SEQUENCE: 38

000

<210> SEQ ID NO 39
<211> LENGTH: 486
<212> TYPE: DNA
<213> ORGANISM: Homo sapiens
<220> FEATURE:
<223> OTHER INFORMATION: HE4 protein (WFDC2) mRNA, complete cds

<400> SEQUENCE: 39
tgagagaaag cggccgcacc ccgcccggca tagcaccatg cctgcttgtc gcctaggccc       60
gctagccgcc gccctcctcc tcagcctgct gctgttcggc ttcaccctag tctcaggcac     120

```
aggagcagag aagactggcg tgtgccccga gctccaggct gaccagaact gcacgcaaga    180
gtgcgtctcg gacagcgaat gcgccgacaa cctcaagtgc tgcagcgcgg gctgtgccac    240
cttctgctct ctgcccaatg ataaggaggg ttcctgcccc caggtgaaca ttaactttcc    300
ccagctcggc ctctgtcggg accagtgcca ggtggacagc cagtgtcctg gccagatgaa    360
atgctgccgc aatggctgtg ggaaggtgtc ctgtgtcact cccaatttct gagctccggc    420
caccaccagg ctgagcagtg aagatagaaa gtttctgcct ggccctgcag cgtgttacag    480
cccacc                                                              486
```

COMPOSITIONS AND METHODS OF USE FOR DETERMINATION OF HE4A

CROSS-REFERENCE TO RELATED APPLICATIONS

This application is a U.S. national stage application filed under 35 U.S.C. §371 of International Application No. PCT/US2011/025321, which was filed on Feb. 17, 2011. The entire content of the prior International Application is hereby incorporated by reference into the present application.

SEQUENCE LISTING

The instant application contains a Sequence Listing which has been submitted in ASCII format via EFS-Web and is hereby incorporated by reference in its entirety. The ASCII copy, created on Aug. 29, 2013, is named D4496-00901_SL.txt and is 16,301 bytes in size.

The invention includes compositions and methods for the detection, diagnosis, grading, staging, prognosis and predicting and monitoring treatment responsiveness of subjects suspected of and/or suffering from ovarian cancer. Also disclosed are immunoassays, binding agents, and antibodies and methods of detecting ovarian cancer by determining the presence of full length HE4a in samples obtained from patients.

BACKGROUND OF THE INVENTION

The WFDC2 (HE4/HE4a) gene product is a member of a family of stable 4-disulfide core proteins. HE4 is a secreted and glycosylated protein that was first observed in human epididymis tissue (human epididymis protein 4; HE4) and is overexpressed in certain cancers, including ovarian cancers. Characterization of the HE4/HE4a proteins and nucleic acids have been reported, for example, in Kirchhoff C, Habben I, Ivell R, Krull N (March 1992). "A major human epididymis-specific cDNA encodes a protein with sequence homology to extracellular proteinase inhibitors". Biol Reprod 45 (2): 350-7 Schummer M, Ng W V, Bumgarner R E, Nelson P S, Schummer B, Bednarski D W, Hassell L, Baldwin R L, Karlan B Y, Hood L (December 1999). "Comparative hybridization of an array of 21,500 ovarian cDNAs for the discovery of genes overexpressed in ovarian carcinomas". Gene 238 (2): 375-85; Kirchhoff C (1998). "Molecular characterization of epididymal proteins." Rev. Reprod. 3 (2): 86-95; Kirchhoff C, Osterhoff C, Habben I, et al. (1990). "Cloning and analysis of mRNAs expressed specifically in the human epididymis." Int. J. Androl. 13 (2): 155-67; Hellström I, et al; Cancer Res. 2003 Jul. 1; 63(13): 3695-700. Over-expression of HE4/HE4a in cancer cells suggests that this protein and its various isoforms can be a useful biomarker for detecting cancer and for identifying patients having an increased likelihood of having cancer. Methods and composition relating to the use of molecular markers such as HE4/HE4a have been reported previously, including U.S. Pat. No. 7,270,960; US20100311099; US20080020473; US20070286865; US20100047818; US20090104684; and US20030108965, the contents of each of which are incorporated herein in their entirety.

HE4/HE4a proteins have been reported to have different isoforms due to alternative splicing as well as different glycoforms from different patterns of glycosylation. In light of the above, a need exists in the art for compositions and binding agents (e.g. antibodies) that are capable of detecting over-expression of biomarkers such as HE4a, their variants, splice isoforms and glycoforms for the diagnosis of cancer.

SUMMARY OF THE INVENTION

The invention includes compositions and methods for diagnosing ovarian cancer in a subject and for identifying subjects with an increased likelihood of having ovarian cancer. The compositions include monoclonal antibodies, their variants and fragments that specifically bind to soluble and cell surface forms of HE4/HE4a that are over-expressed on ovarian carcinoma. Monoclonal antibodies having the binding characteristics of the disclosed HE4a antibody are also provided. Hybridoma cell lines that produce a HE4/HE4a monoclonal antibody are also disclosed. The compositions disclosed have uses in diagnostic methods as well as in screening methods for identifying subjects having an increased likelihood of having ovarian cancer. In particular, diagnostic methods can comprise an immunohistochemistry (IHC) assay or a double sandwich ELISA assay. Kits comprising one or more of the disclosed HE4a monoclonal antibodies and for practicing the methods of the invention are also provided. Polypeptides comprising the amino acid sequence for a HE4a epitope and methods of using these polypeptides in the production of antibodies are also disclosed.

BRIEF SUMMARY OF THE DRAWINGS

FIG. 4 shows the HE4a nucleotide (SEQ ID NO: 6) and peptide (SEQ ID NO: 1) sequences; including the N-WFDC and C-WFDC HE4a domains.

DETAILED DESCRIPTION

Figure 1:
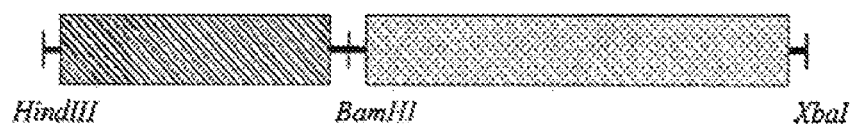
FIG. 1 illustrates an exemplary HE4a fusion protein embodiment comprising a HE4a domain and a Human/Mouse IgG.

Various compositions and methods for diagnosing ovarian cancer in a subject and for identifying subjects with an increased likelihood of having ovarian cancer are provided. Compositions include monoclonal antibodies that are capable of binding to HE4/HE4a, a protein that has been shown to be over-expressed in ovarian cancer cells. The compositions include monoclonal antibodies, and variants and fragments thereof that specifically bind to soluble and cell surface forms of HE4/HE4a that is over-expressed on ovarian carcinoma. Monoclonal antibodies having the binding characteristics of a HE4a antibody of the present disclosure are further provided. Hybridoma cell lines that produce the monoclonal antibodies of the present disclosure are also provided. More particularly, hybridoma cell lines that produce monoclonal antibodies that bind to the N-WFDC domain of HE4a are provided. Kits comprising the monoclonal antibodies described are also disclosed. The invention also includes polypeptides comprising the amino acid sequence for a HE4a epitope and methods of using these polypeptides in the production of antibodies. The compositions find particular use in "sandwich" ELISA methods or IHC for diagnosing ovarian cancer in a subject and in screening methods for identifying subjects with an increased likelihood of having ovarian cancer.

In one aspect, the present disclosure provides a monoclonal antibody capable of specifically binding to HE4a. In one embodiment, the monoclonal antibody is produced by the hybridoma cell line 12A2, deposited with the ECACC as Patent Deposit No. 10091401. The hybridoma cell line 12A2 was deposited at the European Collection of Cell Cultures, Health Protection Agency, Porton Down, Salisbury, UK, on Sep. 14, 2010 under the terms of the Budapest Treaty. In another embodiment, the monoclonal antibody is produced by the hybridoma cell line 14E2, deposited with the ECACC as Patent Deposit No. 11022202. The hybridoma cell line 14E2 was deposited at the European Collection of Cell Cultures. Health Protection Agency, Porton Down, Salisbury, UK, on Feb. 22, 2011 under the terms of the Budapest Treaty. In another embodiment, the monoclonal antibody binds to the amino acid sequence set forth in SEQ ID NO: 17 HE4a N-WFDC (E K T G V C P E L Q A D Q N C T Q E C V S D S E C A D N L K C C S A G C A T F C S L P N D).

In another aspect, the invention provides a kit for diagnosing ovarian cancer comprising a monoclonal antibody that binds to the amino acid sequence set forth in SEQ ID NO:17 HE4a N-WFDC and an additional monoclonal antibody that binds to the amino acid sequence set forth in SEQ ID NO: 19 HE4a C-WFDC. (K E G S C P Q V N I N F P Q L G L C R D Q C Q V D S Q C P G Q M K C C R N G C G K V S C V T P N F). Also provided is a kit for diagnosing ovarian cancer in a patient comprising: a capture antibody immobilized on a solid support, wherein the capture antibody is a first HE4a antibody; and a tag antibody, wherein the tag antibody is a second HE4a antibody that is labeled with a detectable substance; wherein said first or said second HE4a antibody is a monoclonal antibody wherein the monoclonal antibody is produced by the hybridoma cell line 14E2, deposited with the ECACC as Patent Deposit No. 11022202, and/or binds to the amino acid sequence set forth in SEQ ID NO: 17 HE4a N-WFDC (E K T G V C P E L Q A D Q N C T Q E C V S D S E C A D N L K C C S A G C A T F C S L P N D).

The instant disclosure also provides a method for producing an HE4a monoclonal antibody comprising: immunizing an animal with a polypeptide under conditions to elicit an immune response, wherein the polypeptide comprises the amino acid sequence set forth in SEQ ID NOs:1, 3 and 5 (HE4a; HE4a V2; HE4a-V4) and variants thereof; isolating antibody-producing cells from the animal; fusing the antibody-producing cells with immortalized cells in culture to form monoclonal antibody-producing hybridoma cells; culturing the hybridoma cells; and isolating monoclonal antibodies from culture.

The present disclosure also provides for a HE4a binding agent which binds: (a) N-WFDC domain of HE4a; (b) an amino acid sequence encoded by SEQ ID NO:1 HE4a. In one embodiment, the binding agent is an anti-HE4a antibody or HE4a antigen-binding fragment. In a further embodiment, the binding agent selectively binds to HE4a N-WFDC (SEQ ID NO:17). In yet another embodiment, the binding agent is a polyclonal, monoclonal, bispecific, chimeric or humanized antibody or antigen-binding fragment thereof. In another embodiment, the binding agent is labeled with a detectable marker.

The invention also includes a purified amino acid sequence having at least 90% identity to the amino acid sequence of a monoclonal antibody produced by the hybridoma cell line 12A2, deposited with the ECACC as Patent Deposit No. 10091401.

In another aspect, a purified amino acid sequence is provided wherein the sequence having at least 90% identity to the amino acid sequence of a monoclonal antibody is produced by the hybridoma cell line 14E2, deposited with the ECACC as Patent Deposit 14E2 ECACC No. 11022202.

The present disclosure also includes a method for obtaining a nucleic acid sequence encoding a HE4a polypeptide comprising: a) amplifying a nucleic acid from a sample with a primer set comprising a forward and a reverse primer, wherein the primer sets are selected from the group consisting of SEQ ID NO: 21 V4 F and SEQ ID NO: 23_V4 R, SEQ ID NO: 25 V2F and SEQ ID NO: 27 V2R; b) isolating the amplified nucleic acid.

The present invention also includes an isolated nucleic acid molecule encoding a binding protein which binds to the sequence of SEQ ID NO 17 HE4a N-WFDC, wherein the amino acid sequence of the binding protein has at least 90% identity the amino acid sequence of a monoclonal antibody produced by the hybridoma 12A2, deposited with the ECACC as Patent Deposit No. 10091401 or cell line 14E2 deposited with the ECACC as Patent Deposit No. 11022202 and/or binds to the amino acid sequence set forth in SEQ ID NO:17HE4a N-WFDC (E K T G V C P E L Q A D Q N C T Q E C V S D S E C A D N L K C C S A G C A T F C S L P N D).

In another aspect, vectors and host cells comprising the isolated nucleic acid molecule of encoding a binding protein which binds to the sequence of SEQ ID NO 17 HE4a N-WFDC are provided.

The present disclosure also provides an isolated fusion protein comprising a heterologous HE4a polypeptide joined to a Fc receptor polypeptide comprising an amino acid sequence of SEQ ID NO:17 HE4a N-WFDC. In one embodiment, the isolated fusion protein is obtained by nucleic acid amplification using primers encoded by SEQ ID NO: 29 W1F; SEQ ID NO: 31 W1R; SEQ ID NO: 33 W2F, SEQ ID NO: 35 W2R. In another embodiment, the fusion protein comprises a heterologous HE4a antigen polypeptide that is a splice variant.

The invention also includes a method of screening for the presence of a ovarian cancer in a subject comprising: contacting a biological sample from a subject with at least one antibody specific for an HE4a antigen polypeptide to determine the presence in the biological sample of a molecule naturally occurring in soluble form in the sample and having an antigenic determinant that is reactive with at least one antibody, under conditions and for a time sufficient to detect binding of the antibody to the antigenic determinant, and then detecting the presence of a ovarian cancer. In one embodiment, the biological sample is selected from the group consisting of blood, serum, serosal fluid, plasma, lymph, urine, cerebrospinal fluid, saliva, a mucosal secretion, a vaginal secretion, ascites fluid, pleural fluid, pericardial fluid, peritoneal fluid, abdominal fluid, culture medium, conditioned culture medium and lavage fluid.

The present disclosure further provides a method of screening for the presence of a ovarian cancer in a subject comprising: contacting a biological sample comprising a cell from a subject with at least one antibody specific for an HE4a antigen polypeptide to determine the presence in the biological sample of a cell surface molecule having an antigenic determinant that is reactive with at least one antibody, under conditions and for a time sufficient to detect binding of the antibody to the antigenic determinant, and thus detecting the presence of a ovarian cancer. In one embodiment, the antibody is detectably labeled. In another embodiment, the antibody is not detectably labeled and where the detection of binding of the antibody to an antigenic determinant is indirect.

The invention also includes a method of screening for the presence of an ovarian cancer in a subject comprising: contacting a biological sample from the subject with at least one immobilized first antibody specific for a HE4a antigen polypeptide to determine the presence of a molecule in the sample, under conditions and for a time sufficient to specifically bind the first antibody to HE4a antigen polypeptide and thereby form an immune complex; removing constituents of the sample that do not specifically bind to the first antibody; and contacting the immune complex with at least one second antibody specific for a HE4a antigen polypeptide, wherein the antigen combining site of the second antibody does not competitively inhibit the antigen combining site of the immobilized first antibody, under conditions and for a time sufficient to detect specific binding of the second antibody to the HE4a antigen polypeptide, and thus detecting the presence of an ovarian cancer. In one embodiment, the immobilized first antibody is selected from the group consisting of 12A2, 14E2, 2H5 and 3D8. In one embodiment, the second antibody is selected from the group consisting of 12A2, 14E2, 2H5, and 3D8. In another embodiment the immobilized first antibody is 14E2. In yet another embodiment, the second antibody is 12A2.

Also disclosed is a method of diagnosing a subject with ovarian cancer comprising: detecting HE4a antigen in a test sample from the subject; contacting the test sample with an antibody having an antigen binding domain which binds to HE4a N-WFDC for a time and under conditions sufficient for the formation of antibody/antigen complexes; and detecting presence of the complexes on a display wherein presence of the complexes indicating presence of HE4a in the test sample is correlated with presence of ovarian cancer. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

The invention also includes a method of diagnosing a subject with ovarian cancer comprising: detecting HE4a antigen in a test sample from the subject; contacting the test sample with a first antibody having an antigen binding domain which binds to amino acids N-WFDC of HE4a for a time and under conditions sufficient for the formation of first antibody/antigen complexes; adding a conjugate to the first antibody/antigen complexes, wherein the conjugate comprises a second antibody attached to a signal generating compound capable of generating a detectable signal, for a time and under conditions sufficient to form first antibody/antigen/second antibody complexes; and detecting presence of a signal generating by the signal generating compound on a display wherein presence of the signal indicating presence of HE4a antigen in the test sample is correlated with presence of ovarian cancer. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

The present disclosure also includes a method of prognosis for a subject with ovarian cancer comprising: detecting HE4a antigen in a test sample from the subject; contacting the test sample with an antibody having an antigen binding domain which binds to HE4a N-WFDC for a time and under conditions sufficient for the formation of antibody/antigen complexes; and detecting presence of the complexes on a display wherein the presence of the complexes indicating presence of HE4a antigen in the test sample is correlated with stages of ovarian cancer. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

The invention also includes a method of prognosis for a subject with ovarian cancer comprising: detecting HE4a antigen in a test sample from the subject; contacting the test sample with a first antibody having an antigen binding domain which binds to amino acids N-WFDC of HE4a for a time and under conditions sufficient for the formation of first antibody/antigen complexes; adding a conjugate to the first antibody/antigen complexes, wherein the conjugate comprises a second antibody attached to a signal generating compound capable of generating a detectable signal, for a time and under conditions sufficient to form first antibody/antigen/second antibody complexes; and detecting presence of a signal generated by the signal generating compound on a display wherein the presence of the signal indicating presence of HE4a antigen in the test sample is correlated with stages of ovarian cancer. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

Also disclosed is a method of monitoring a subject undergoing treatment for ovarian cancer comprising: detecting HE4a antigen in a test sample from the subject; contacting the test sample with an antibody having an antigen binding domain which binds to HE4a N-WFDC for a time and under conditions sufficient for the formation of antibody/antigen complexes; and detecting presence of the complexes on a display wherein the presence of the complexes indicating presence of HE4a antigen in the test sample is correlated with the responsiveness to the treatment. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

The present disclosure further provides a method of monitoring a subject undergoing treatment for ovarian cancer comprising: detecting HE4a antigen in a test sample from the subject; contacting the test sample with a first antibody having an antigen binding domain which binds to amino acids N-WFDC of HE4a for a time and under conditions sufficient for the formation of first antibody/antigen complexes; adding a conjugate to the first antibody/antigen complexes, wherein the conjugate comprises a second antibody attached to a signal generating compound capable of generating a detectable signal, for a time and under conditions sufficient to form first antibody/antigen/second antibody complexes; and detecting presence of a signal generated by the signal generating compound on a display wherein the presence of the signal indicating presence of HE4a antigen in the test sample is correlated with responsiveness to the treatment. In one embodiment, the antibody comprises an antigen-binding domain that binds to amino acids N-WFDC of HE4a. In another embodiment, the antibody is a monoclonal antibody produced by a hybridoma cell line having ECACC as Patent Deposit No. 10091401.

The current invention also provides a method for detecting the presence or absence of a ovarian cancer in a patient, comprising: contacting a test ovarian tissue sample obtained from the subject with an antibody that specifically binds to the polypeptide set forth in any of SEQ ID NOS: 1, 3, 5, 7, 9, 11, 13 or 15 (HE4) detecting an amount of the antibody that binds to the polypeptide in the test ovarian cancer tissue sample; and comparing the amount of the antibody that binds to the polypeptide in the test ovarian cancer tissue sample to a predetermined cut-off value, wherein the test ovarian cancer tissue sample is positive for ovarian cancer when the amount of antibody that binds to the polypeptide in the test ovarian tissue sample is above the predetermined cut-off value, thereby detecting the presence or absence of an ovarian cancer in the subject. In one embodiment, the amount of antibody that binds to the polypeptide in the test ovarian cancer tissue sample is determined using immunohistochemistry.

The methods disclosed herein pertain to HE4/HE4a, a member of the "four-disulfide core" family of proteins as described. The "four-disulfide core" family of proteins comprises a heterogeneous group of small acid- and heat-stable molecules of divergent function and which includes human epididymal four-disulfide core protein, or "HE4" (Kirchhoff et al., 1991 Biol. Reprod. 45:350-357; Wang et al., 1999 Gene 229:101; Schummer et al., 1999 Gene 238:375). HE4 cDNA was first isolated from human epididymis (Kirchhoff et al., 1991 Biol. Reprod. 45:350-357), and HE4 cDNA was later detected with high frequency in cDNA libraries constructed from ovarian carcinomas (Wang et al., 1999 Gene 229:101; Schummer et al., 1999 Gene 238:375). The revised sequence of HE4a was disclosed in Hellström et al., 2003, Canc. Res. 63:3695-3700 and in U.S. Pat. No. 7,270,960. HE4a exhibits an amino acid sequence that is highly similar to, but distinct from, the deduced sequence of the molecule that was referred to as HE4 in earlier publications.

A number of isoforms of the HE4 protein have been reported as detailed in Table 1 below. One of skill in the art will appreciate that a HE4/HE4a monoclonal antibody of the present disclosure may bind to more than one HE4 isoform so long as each isoform includes the relevant epitope sequence for the particular HE4/HE4a antibody.

TABLE 1

HE4 ISOFORMS

| HE4 Isoform | Accession No. | Sequence Identifier |
|---|---|---|
| 1 | NP_006094 | SEQ ID NO: 1 |
| 2 | AAL37488 | SEQ ID NO: 3 |
| 3 | AAL37487 | SEQ ID NO: 5 |
| 4 | AAL37486 | SEQ ID NO: 7 |
| 5 | AAL37485 | SEQ ID NO: 9 |
| 6 | AAH46106 | SEQ ID NO: 11 |
| 7 | AAO52683 | SEQ ID NO: 13 |
| 8 | CAA44869 | SEQ ID NO: 15 |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and humans.

The methods disclosed herein also include compositions and methods for detection of cell surface and/or soluble forms of HE4a that occur naturally in subjects, including elevated levels of such polypeptides in subjects having certain cancers. This disclosure therefore provides useful compositions and methods for the detection and diagnosis of a malignant condition (e.g. ovarian cancer) in a subject by specific detection of such cell surface and/or soluble HE4a polypeptides.

Also provided is the design of immunoassays and generation of monoclonal antibodies for the determination of full length HE4a antigen and the use of the immunoassays and monoclonal antibodies for serological diagnosis of ovarian cancer, monitoring the clinical course of the disease and diagnosis of ovarian cancer by tissue analysis of HE4a.

Establishment of novel monoclonal antibodies against epitopes specific of the HE4a N-WFDC domain, and combining these antibodies with antibodies against HE4a C-WFDC domain made it possible to design specific immunoassays for determination of the full length HE4a.

According to the methods disclosed herein, a human HE4a antigen polypeptide (or HE4a polypeptide) can be detected in a biological sample from a subject or biological source. Biological samples can be provided by obtaining a blood sample, biopsy specimen, tissue explant, organ culture, biological fluid or any other tissue or cell preparation from a subject or a biological source. The subject or biological source can be a human or non-human animal, a primary cell culture or culture adapted cell line including but not limited to genetically engineered cell lines that can contain chromosomally integrated or episomal recombinant nucleic acid sequences, immortalized or immortalizable cell lines, somatic cell hybrid cell lines, differentiated or differentiable cell lines, transformed cell lines and the like. In certain embodiments of the methods disclosed herein, the subject or biological source can be suspected of having or being at risk for having an ovarian cancer.

In some embodiments, the biological sample includes at least one cell from a subject or biological source, and in other embodiments the biological sample is a biological fluid containing another tumor marker. Biological fluids are typically liquids at physiological temperatures and can include naturally occurring fluids present in, withdrawn from, expressed or otherwise extracted from a subject or biological source. Certain biological fluids derive from particular tissues, organs or localized regions and certain other biological fluids can be more globally or systemically situated in a subject or biological source. Non-limiting examples of biological fluids include blood, serum and serosal fluids, plasma, lymph, urine, cerebrospinal fluid, saliva, serosal fluids, plasma, lymph, mucosal secretions of the secretory tissues and organs, vaginal secretions, breast milk, tears, and ascites fluids such as those associated with non-solid tumors—are also suitable. Additional examples include fluids of the pleural, pericardial, peritoneal, abdominal and other body cavities, and the like. Biological fluids can further include liquid solutions contacted with a subject or biological source, for example, cell and organ culture medium including cell or organ conditioned medium, lavage fluids and the like. In other embodiments the biological sample is a cell-free liquid solution, such as blood serum, plasma, or the supernatant of centrifuged urine.

In certain other embodiments the biological sample comprises an intact cell, and in certain other preferred embodiments the biological sample comprises a cell extract containing a nucleic acid sequence encoding a HE4a antigen polypeptide or a fragment or variant thereof. In still other embodiments of the methods disclosed herein, it is desired that cells are physically or chemically ruptured or lysed before assaying to provide cell contents for analysis.

As used herein, a "molecule naturally occurring in soluble form" in a sample may be a soluble protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or any combination thereof such as, for example, a glycoprotein, a glycolipid, a lipoprotein, a proteolipid, or any other biological molecule that is a soluble or cell-free constituent of a biological sample as provided herein. A "molecule naturally occurring in soluble form" further refers to a molecule that is in solution or present in a biological sample, including a biological fluid as provided herein, and that is not bound to the surface of an intact cell. For example, a molecule naturally occurring in soluble form may include but need not be limited to a solute; a component of a macromolecular complex; a material that is shed, secreted or exported from a cell; a colloid; a microparticle or nanoparticle or other fine suspension particle; or the like.

The presence of a malignant condition (e.g. ovarian cancer) in a subject refers to the presence of dysplastic, cancerous and/or transformed cells in the subject, including, for example neoplastic, tumor, non-contact inhibited or oncogenically transformed cells, or the like. By way of illustration and not limitation, in the context of the methods disclosed herein a malignant condition may refer further to the presence in a subject of cancer cells that are capable of secreting, shedding, exporting or releasing a HE4a antigen polypeptide (or a HE4a polypeptide) in such a manner that elevated levels of such a polypeptide are detectable in a biological sample from the subject. In some embodiments, for example, such cancer cells are malignant epithelial cells such as carcinoma cells, and in some embodiments such cancer cells are malignant mesothelioma cells, which are transformed variants of squamous cell epithelial or mesothelial cells that are found, for example, lining pleural, pericardial, peritoneal, abdominal and other body cavities.

In one embodiment, ovarian tumor cells, the presence of which signifies the presence of an ovarian cancer, can include primary and metastatic ovarian cancer cells. Criteria for classifying a malignancy as are well known in the art as are the establishment and characterization of human ovarian carcinoma cell lines from primary and metastatic tumors. In other embodiments, the present disclosure also contemplates that malignant condition may be mesothelioma, pancreatic carcinoma, non-small cell lung carcinoma or another form of cancer, including any of the various carcinomas such as squamous cell carcinomas and adenocarcinomas, and also including sarcomas and hematologic malignancies (e.g., leukemias, lymphomas, myelomas, etc.). Classification of these and other malignant conditions is known to those having familiarity with the art, and the present disclosure provides determination of the presence of a HE4a polypeptide in such a malignant condition without undue experimentation.

Reference values are provided in the examples contained herein. Such values are suitable for practice of the methods disclosed herein. However it should be noted that the use of the methods disclosed herein is not limited to those reference values or that data. Those skilled in the art can obtain a reference value for their particular needs. Such a reference value can be obtained by analyzing HE4 expression in patients as they undergo biopsy procedures for ovarian cancer masses suspected of being malignant. Methods of obtaining such reference values are provided in the examples. In addition, other reference values may be obtained to focus on specific categories of patients. In is foreseen that such categories could include age, genetic background, risk of cancer, medical history, blood type, physical characteristics such as body mass, and other categories.

As provided herein, the method of screening for the presence of a malignant condition in a subject can employ an antibody specific for a HE4a antigen polypeptide or an antibody specific for a HE4a polypeptide. Antibodies that are specific for a HE4a antigen polypeptide (or a HE4a polypeptide) are readily generated as monoclonal antibodies or as polyclonal antisera, or can be produced as genetically engineered immunoglobulins (Ig) that are designed to have desirable properties using methods well known in the art. For example, by way of illustration and not limitation, antibodies can include recombinant IgGs, chimeric fusion proteins having immunoglobulin derived sequences or "humanized" antibodies (see, e.g., U.S. Pat. Nos. 5,693,762; 5,585,089; 4,816,567; 5,225,539; 5,530,101) that can all be used for detection of a human HE4a polypeptide according to the methods disclosed herein. Such antibodies can be prepared as provided herein, including by immunization with HE4a polypeptides as described below. For example, nucleic acid sequences encoding HE4a polypeptides are disclosed, such that those skilled in the art can routinely prepare these polypeptides for use as immunogens. For instance, monoclonal antibodies such as 12A2, 14E2, 2H5, and 3D8 and, which are described in greater detail below, can be used to practice certain methods according to the methods disclosed herein.

The term "antibodies" includes polyclonal antibodies, monoclonal antibodies, fragments thereof such as F(ab')$_2$, and Fab fragments, as well as any naturally occurring or recombinantly produced binding partners, which are molecules that specifically bind a HE4a polypeptide. Antibodies are defined to be "immunospecific" or specifically binding if they bind HE4a polypeptide with a $K_a$ of greater than or equal to about $10^4$-$M^{-1}$ preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of binding partners or antibodies can be readily determined using conventional techniques. Determination of other proteins as binding partners of a HE4a polypeptide can be performed using any of a number of known methods for identifying and obtaining proteins that specifically interact with other proteins or polypeptides, for example, a yeast two-hybrid screening system such as that described in for example, U.S. Pat. No. 5,283,173 and U.S. Pat. No. 5,468,614. The methods disclosed herein also include the use of a HE4a polypeptide, and peptides based on the amino acid sequence of a HE4a polypeptide, to prepare binding partners and antibodies that specifically bind to a HE4a polypeptide.

Antibodies can generally be prepared by any of a variety of techniques known to those of ordinary skill in the art. In one such technique, an immunogen comprising a HE4a polypeptide, for example a cell having a HE4a polypeptide on its surface or an isolated HE4a polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the HE4a polypeptide can then be purified from such antisera by, for example, affinity chromatography using the polypeptide coupled to a suitable solid support.

Monoclonal antibodies specific for HE4a polypeptides or variants thereof can be prepared by any technique known to those skilled in the art. For example, these methods may involve the preparation of immortal cell lines capable of producing antibodies having the desired specificity. Such cell lines can be produced, for example, from spleen cells obtained from an animal immunized as described above. The spleen cells are then immortalized by, for example, fusion with a myeloma cell fusion partner, such as one that is syngeneic with the immunized animal. For example, the spleen cells and myeloma cells can be combined with a membrane fusion promoting agent such as polyethylene glycol or a nonionic detergent for a few minutes, and then plated at low density on a selective medium that supports the growth of hybrid cells, but not myeloma cells. An example of a selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferable, Hybridomas that generate monoclonal antibodies that specifically bind to HE4a polypeptides are contemplated by the methods disclosed herein.

Monoclonal antibodies can be isolated from the supernatants of growing hybridoma colonies. In addition, various techniques can be employed to enhance the yield, such as injection of the hybridoma cell line into the peritoneal cavity of a suitable vertebrate host, such as a mouse or other suitable host. Monoclonal antibodies can then be harvested from the ascites fluid or the blood. Contaminants can be removed from the antibodies by conventional techniques, such as chromatography, gel filtration, precipitation, and extraction. For example, antibodies can be purified by chromatography on immobilized Protein G or Protein A using standard techniques.

Within certain embodiments, the use of antigen-binding fragments of antibodies can be used. Such fragments include Fab fragments, which can be prepared using standard techniques (e.g., by digestion with papain to yield Fab and Fc fragments). The Fab and Fe fragments can be separated by affinity chromatography (e.g., on immobilized protein A columns), using standard techniques. Such techniques are well known in the art, see, e.g., Weir, D. M., Handbook of Experimental Immunology, 1986, Blackwell Scientific, Boston.

In certain aspects, HE4 fusion proteins are provided. Multifunctional fusion proteins having specific binding affinities for pre-selected antigens by virtue of immunoglobulin V-region domains encoded by DNA sequences linked in-frame to sequences encoding various effector proteins are known in the art, for example, as disclosed in EP-B1-0318554, U.S. Pat. No. 5,132,405, U.S. Pat. No. 5,091,513 and U.S. Pat. No. 5,476,786. Such effector proteins include polypeptide domains that can be used to detect binding of the fusion protein by any of a variety of techniques with which those skilled in the art will be familiar, including but not limited to a biotin mimetic sequence, direct covalent modification with a detectable labeling moiety, noncovalent binding to a specific labeled reporter molecule, enzymatic modification of a detectable substrate or immobilization (covalent or non-covalent) on a solid-phase support.

Single chain antibodies for use in the methods disclosed herein can also be generated and selected by a method such as phage display (see by way of example, U.S. Pat. No. 5,223,409). Briefly, in this method, DNA sequences can be inserted into the gene III or gene VIII gene of a filamentous phage, such as M13. Several vectors with multicloning sites have been developed for insertion (McLafferty, M. A., Kent, K. A., Ladner, R. C. & Markland, W. Gene 128, 29-36 (1993); Scott J K, Smith G P. Searching for peptide ligands with an epitope library. Science. 1990 Jul. 27; 249(4967): 386-390; Smith G P, Scott J K. Libraries of peptides and proteins displayed on filamentous phage. Methods Enzymol. 1993; 217:228-257). The inserted DNA sequences can be randomly generated or can be variants of a known binding domain for binding to a HE4a polypeptide. The peptide encoded by the inserted sequence is displayed on the surface of the bacteriophage. Bacteriophage expressing a binding domain for a HE4a polypeptide are selected by binding to an immobilized HE4a polypeptide, for example a recombinant polypeptide prepared using methods well known in the art and nucleic acid coding sequences as disclosed herein. Unbound phage are removed by a wash, typically containing 10 mM Tris, 1 mM EDTA, and without salt or with a low salt concentration. Bound phage are eluted with a salt containing buffer, for example. The NaCl concentration is increased in a step-wise fashion until all the phage are eluted. Typically, phage binding with higher affinity will be released by higher salt concentrations. Eluted phage are propagated in the bacteria host. Further rounds of selection can be performed to select for a few phage binding with high affinity. The DNA sequence of the insert in the binding phage is then determined. Once the predicted amino acid sequence of the binding peptide is known, sufficient peptide for use herein as an antibody specific for a HE4a polypeptide can be made either by recombinant means or synthetically. Recombinant means are used when the antibody is produced as a fusion protein. The peptide can also be generated as a tandem array of two or more similar or dissimilar peptides, in order to maximize affinity or binding.

In the instant disclosure, various assay formats are provided. To detect an antigenic determinant reactive with an antibody specific for a HE4a polypeptide, the detection reagent is typically an antibody, which can be prepared as described herein or by any of a variety of methods known in the art. There are a variety of assay formats known to those of ordinary skill in the art for using an antibody to detect a polypeptide in a sample, including but not limited to enzyme linked immunosorbent assay (ELISA), radioimmunoassay (RIA), immunofluorimetry, immunoprecipitation, equilibrium dialysis, immunodiffusion and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston. For example, the assay may be performed in a Western blot format, wherein a protein preparation from the biological sample is submitted to gel electrophoresis, transferred to a suitable membrane and allowed to react with the antibody. The presence of the antibody on the membrane can then be detected using a suitable detection reagent, as is well known in the art and described below.

In another embodiment, the assay involves the use of an antibody immobilized on a solid support to bind to the target HE4a polypeptide and remove it from the remainder of the sample. The bound HE4a polypeptide may then be detected using a second antibody reactive with a distinct HE4a polypeptide antigenic determinant, for example, a reagent that contains a detectable reporter moiety. As a non-limiting example, according to this embodiment the immobilized antibody and the second antibody which recognize distinct antigenic determinants may be two of the exemplary monoclonal antibodies 2H5 and 3D8. Alternatively, a competitive assay may be utilized, in which a HE4a polypeptide is labeled with a detectable reporter moiety and allowed to bind to the immobilized HE4a polypeptide specific antibody after incubation of the immobilized antibody with the sample. The extent to which components of the sample inhibit the binding of the labeled polypeptide to the antibody is indicative of the reactivity of the sample with the immobilized antibody, and as a result, indicative of the level of HE4a in the sample.

The solid support may be any material known to those of ordinary skill in the art to which the antibody may be attached, such as a test well in a microtiter plate, a nitrocellulose filter or another suitable membrane. Alternatively the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of HE4a antigen polypeptide in a sample is a two-antibody sandwich assay. This assay may be performed by first contacting a HE4a polypeptide-specific antibody (e.g., a monoclonal antibody such as 12A2, 14E2, 2H5 and 3D8) that has been immobilized on a solid support, commonly the well of a microliter plate, with the biological sample, such that a soluble molecule naturally occurring in the sample and having an antigenic determinant that is reactive with the antibody is allowed to bind to the immobilized antibody (e.g., a 30 minute incubation time at room temperature is generally sufficient) to form an antigen-antibody complex or an immune complex. Unbound constituents of the sample are then removed from the immobilized immune complexes. Next, a second antibody specific for a HE4a antigen polypeptide is added, wherein the antigen combining site of the second antibody does not competitively inhibit binding of the antigen combining site of the immobilized first antibody to a HE4a polypeptide (e.g., a monoclonal antibody such as 2H5 or 3D8 that is not the same as the monoclonal antibody immobilized on the solid support). The second antibody can be detectably labeled as provided herein, such that it can be directly detected. Alternatively, the second antibody can be indirectly detected through the use of a detectably labeled secondary (or "second stage") anti-antibody, or by using a specific detection reagent as provided herein. The methods disclosed herein are not limited to any particular detection procedure, as those having familiarity with immunoassays will appreciate that there are numerous reagents and configurations for immunologically detecting a particular antigen in a two-antibody sandwich immunoassay.

In certain embodiments of the methods disclosed herein using the two-antibody sandwich assay described above, the first, immobilized antibody specific for a HE4a antigen polypeptide is a polyclonal antibody and the second antibody specific for a HE4a antigen polypeptide is a polyclonal antibody. Any combination of non-competitive HE4a antibodies could be used with the methods disclosed herein. Including monoclonal antibodies, polyclonal antibodies and combinations thereof. In certain other embodiments of the methods disclosed herein the first, immobilized antibody specific for a HE4a antigen polypeptide is a monoclonal antibody and the second antibody specific for a HE4a antigen polypeptide is a polyclonal antibody. In certain other embodiments of the methods disclosed herein the first, immobilized antibody specific for a HE4a antigen polypeptide is a polyclonal antibody and the second antibody specific for a HE4a antigen polypeptide is a monoclonal antibody. In certain other highly preferred embodiments of the methods disclosed herein the first, immobilized antibody specific for a HE4a antigen polypeptide is a monoclonal antibody and the second antibody specific for a HE4a antigen polypeptide is a monoclonal antibody. For example, in these embodiments it should be noted that monoclonal antibodies 12A2, 14E2, 2H5 and 3D8 as provided herein recognize distinct and noncompetitive antigenic determinants (e.g., epitopes) on HE4a polypeptides, such that any pairwise combination of these monoclonal antibodies can be employed. In particular, certain combinations are useful in detecting specific full length 11E4 variants or splice variants. In other embodiments of the methods disclosed herein the first, immobilized antibody specific for a HE4a antigen polypeptide and/or the second antibody specific for a HE4a antigen polypeptide can be any of the kinds of antibodies known in the art and referred to herein, for example by way of illustration and not limitation, Fab fragments, F(ab')$_2$ fragments, immunoglobulin V-region fusion proteins or single chain antibodies. Those familiar with the art will appreciate that the methods disclosed herein encompass the use of other antibody forms, fragments, derivatives and the like in the methods disclosed and claimed herein.

In certain embodiments, the second antibody can contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of antibody remaining on the support after wash. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (by way of example, see Scouten, W. H. (1987) A survey of enzyme coupling techniques. Methods in Enzymology 135, 30-65). Spectroscopic method can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well-known techniques.

In another embodiment, the methods disclosed herein contemplate the use of a HE4a antigen polypeptide as provided herein to screen for the presence of an ovarian cancer by detection of immunospecifically reactive antibodies in a biological sample from a biological source or subject. According to this embodiment, a HE4a antigen polypeptide (or a fragment or variant thereof including a truncated HE4a antigen polypeptide as provided herein) is detectably labeled and contacted with a biological sample to detect binding to the HE4a antigen polypeptide of an antibody naturally occurring in soluble form in the sample. For example, the HE4a antigen polypeptide can be labeled biosynthetically by using the sequences disclosed herein in concert with well known methods such as incorporation during in vitro translation of a readily detectable (e.g. radioactively labeled) amino acid, or by using other detectable reporter moieties such as those described above. One skilled in the art would readily appreciate that this embodiment of the methods contemplates that certain HE4a polypeptides such as the HE4a fusion polypeptides disclosed herein can provide peptides that are particularly immunogenic and so give rise to specific and detectable antibodies. For example, according to this theory certain HE4a fusion polypeptides can represent "non-self" antigens that provoke an avid immune response, while HE4a polypeptides that lack fusion domains can be viewed by the immune system as more resembling "self" antigens that do not readily elicit humoral or cell-mediated immunity.

A method of screening for the presence of a malignant condition according to the methods disclosed herein can be further enhanced by the detection of more than one tumor associated marker in a biological sample from a subject. Accordingly, the methods disclosed provide a way of screening that, in addition to detecting reactivity of a naturally occurring component with an antibody specific for a HE4a antigen polypeptide, also includes detection of at least one additional soluble marker of a malignant condition using established methods known in the art as well as those disclosed. As noted above, there are currently a number of soluble tumor associated antigens that are detectable in samples of readily obtained biological fluids.

Exemplary screening methods for identifying patients with an increased likelihood of having ovarian cancer generally comprise detecting in a patient body sample expression of a plurality of biomarkers that are selectively over-expressed in ovarian cancer. Over-expression of the biomarkers is indicative of an increased likelihood that the patient has ovarian cancer. The methods of the present disclosure may comprise, for example, a "two-step" analysis, wherein a first assay step is performed to detect the expression of a first biomarker (e.g., HE4/HE4a) or panel of biomarkers. If the first biomarker or panel of biomarkers is overexpressed, a second assay step is performed to detect the expression of a second biomarker or panel of biomarkers. Over-expression of the first and second biomarkers or panels of biomarkers is indicative of an increased likelihood that the patient has ovarian cancer.

Alternatively, nucleic acid sequences encoding HE4a polypeptides can be detected, using standard hybridization and/or polymerase chain reaction (PCR) techniques. Suitable probes and primers can be designed by those of ordinary skill in the art based on the HE4a cDNA sequences provided herein. Assays can generally be performed using any of a variety of samples obtained from a biological source, such as eukaryotic cells, bacteria, viruses, extracts prepared from such organisms and fluids found within living organisms.

Standard recombinant DNA and molecular cloning techniques used in the examples are well known in the art.

From the physicochemical and immunochemical properties of HE4a polypeptides disclosed herein, and using the presently disclosed nucleic acid sequences encoding HE4a, a person having ordinary skill in the art may also prepare a recombinant HE4a polypeptide that can be used to produce and characterize specific antibodies according to well known methodologies. HE4a polypeptides can be expressed in mammalian cells, yeast, bacteria, or other cells under the control of appropriate promoters. Cell-free translation systems can also be employed to produce such proteins using RNAs derived from the HE4a polypeptide DNA coding regions disclosed herein. Appropriate cloning and expression vectors for use with prokaryotic and eukaryotic hosts have been previously described and are well known by those skilled in the art. In preferred embodiments of the invention, HE4a polypeptides are expressed in mammalian cells.

The present invention therefore provides an isolated nucleic acid molecule that encodes a HE4a antigen polypeptide or a nucleic acid molecule capable of hybridizing to such an HE4a polypeptide-encoding nucleic acid, or a nucleic acid molecule having a sequence complementary thereto.

Variants preferably exhibit at least about 70% identity, more preferably at least about 80%-85% identity and most preferably at least about 90%, 92%, 94%, 95%, 96%, 97%, 98% or 99% identity to a polynucleotide sequence that encodes a native HE4a antigen polypeptide or a portion thereof. The percent identity may be readily determined by comparing sequences using computer algorithms well known to those of ordinary skill in the art, such as Align or the BLAST algorithm (Altschul S. F. (1991) Amino acid substitution matrices from an information theoretic perspective. Journal of Molecular Biology 219: 555-565; Henikoff S, Henikoff J G. 0992) Amino acid substitution matrices from protein blocks. Proc Natl Acad Sci USA, which is available at the NCBI website.

Certain variants are substantially homologous to a native gene. Such polynucleotide variants are capable of hybridizing under moderately stringent conditions to a naturally occurring DNA or RNA sequence encoding a native HE4a antigen (or a complementary sequence). Suitable moderately stringent conditions include, for example, the following steps or their equivalent: prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS. For additional stringency, conditions may include, for example, a wash in 0.1×SSC and 0.1% SDS at 60° C. for 15 minutes, or the equivalent. A person having ordinary skill in the art will readily appreciate the parameters that may be varied as a routine matter to create appropriately stringent hybridization conditions that are in some way selective for a particular nucleic acid of interest, and will further appreciate that such conditions may be a function of the particular nucleic acid sequences involved in the hybridization.

The nucleic acids which encode HE4a polypeptides, or any other HE4a polypeptides for use according to the invention, may include, but are not limited to: only the coding sequence for the HE4a polypeptide; the coding sequence for the HE4a polypeptide and additional coding sequence; the coding sequence for the HE4a polypeptide (and optionally additional coding sequence) and non-coding sequence, such as introns or non-coding sequences 5' and/or 3' of the coding sequence for the HE4a polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding an HE4a polypeptide" encompasses a nucleic acid that includes only coding sequence for the polypeptide as well as a nucleic acid including additional coding and/or non-coding sequence(s).

The present invention further relates to variants of the herein described nucleic acids which encode for fragments, analogs and derivatives of an HE4a polypeptide, for example the human HE4a polypeptides having the deduced amino acid sequence of any of SEQ ID NOS: 1, 3, 5, 7, 9, 11, 13 or 15 (HE4). The variants of the nucleic acids encoding HE4a may be naturally occurring allelic or splice variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded HE4a polypeptide. Variants and derivatives of HE4a may be obtained by mutations of nucleotide sequences encoding HE4a polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion as is well known to those skilled in the art.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. By way of example, EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

The appropriate DNA sequence(s) may be inserted into any of a number of well known vectors appropriate for the selected host cell by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art.

Examples of mammalian expression systems include the COS-7 lines of monkey kidney fibroblasts, described by Gluzman Y. SV40-transformed simian cells support the replication of early SV40 mutants. Cell. 1981 January; 23(1):175-82, and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived, for example, from SV40 splice and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis, L. G., Dibner, M. D. and Battey, J. F.: Basic Methods in Molecular Biology. Elsevier, New York, 1986).

The HE4a polypeptide of the invention may be an unmodified polypeptide or may be a polypeptide that has been posttranslationally modified, for example by glycosylation, phosphorylation, fatty acylation including glycosylphosphatidylinositol anchor modification or the like, phospholipase cleavage such as phosphatidylinositol-specific phospholipase c mediated hydrolysis or the like, protease cleavage, dephosphorylation or any other type of protein posttranslational modification such as a modification involving formation or cleavage of a covalent chemical bond.

The terms "fragment," "derivative" and "analog" when referring to HE4a polypeptides, HE4a antigen polypeptides or HE4a fusion proteins, refers to any HE4a polypeptide that retains essentially the same biological function and/or activity as such polypeptide. Thus, an analog may include a HE4a antigen polypeptide isoform such as a differentially post-translationally modified HE4a polypeptide or a variant such as a splice variant. As is well known in the art, a "splice variant" includes variant or alternative forms of a polypeptide that arise from the differential intracellular processing of an RNA transcript. For example, two distinct mRNA species may be splice variants of one another where they differ only by the inclusion of all or a portion of a sequence corresponding to a particular exon in one mRNA species and its absence from the other species. As those familiar with the art will appreciate, other structural relationships can exist between mRNA species that would be generally regarded as splice variants. A HE4a polypeptide further includes a proprotein which can be activated by cleavage of the proprotein portion to produce an active HE4a polypeptide.

Biological functions and/or activities of fragments, derivatives and analogs of HE4a polypeptides or of HE4a antigen polypeptides include, but need not be limited to, the use of such polypeptides as markers in a method of screening for the presence of a malignant condition in a subject as disclosed herein. For example, by detecting in a sample from the subject a molecule naturally occurring in soluble form and having an antigenic determinant that is reactive with at least one antibody specific for a HE4a polypeptide, one skilled in the art may be monitoring a biological function and/or activity of a HE4a polypeptide. Further, it should be noted that in certain embodiments the subject invention method of screening is directed to comparing relative quantities, levels and/or amounts of a detectable molecule naturally occurring in soluble form and having an antigenic determinant that is reactive with at least one antibody specific for a HE4a polypeptide in each of (i) a first biological sample from a first subject suspected of having a malignant condition, and (ii) a second biological sample from a second subject known to be free of a malignant condition. Accordingly, the relative quantitative presence of a HE4a polypeptide in a biological sample may be a biological function and/or activity of a HE4a polypeptide, although such function and/or activity should not be so limited.

A fragment, derivative or analog of a HE4a polypeptide may be (i) one in which one or more of the amino acid residues are substituted with a conserved or non-conserved amino acid residue (preferably a conserved amino acid residue); (ii) one in which additional amino acids are fused to the HE4a polypeptide, including amino acids that may be employed for purification of the HE4a polypeptide or a proprotein sequence; or (iii) a truncated HE4a polypeptide. Such fragments, derivatives and analogs are deemed to be within the scope of those skilled in the art from the teachings herein.

A truncated HE4a polypeptide may be any HE4a polypeptide molecule that comprises less than a full-length version of the HE4a polypeptide. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences. In other preferred embodiments, truncated molecules are polypeptides that comprise less than the full-length amino acid sequence of a particular protein.

As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues.

As known in the art "similarity" between two polypeptides is determined by comparing the amino acid sequence and conserved amino acid substitutes thereto of the polypeptide to the sequence of a second polypeptide. Similarity between two polypeptide or nucleotide sequences, or even the percent identity, may be readily determined by comparing sequences using computer algorithms well known to those of ordinary skill in the art, such as the BLAST algorithm. Examples of other useful computer algorithms are those used in programs such as Align and FASTA, which may be accessed, for example, at the Genestream internet website of the Institut de Genetique Humaine, Montpellier, France (www2.igh.cnrs.fr/home.eng.html). Fragments or portions of the polypeptides of the present invention may be employed for producing the corresponding full-length polypeptide by peptide synthesis; therefore, the fragments may be employed as intermediates for producing the full-length polypeptides.

The term "isolated" means that the material is removed from its original environment (e.g., the natural environment if it is naturally occurring). For example, a naturally occurring polypeptide or polynucleotide present in a living animal is not isolated, but the same polypeptide or polynucleotide, separated from some or all of the co-existing materials in the natural system, is isolated. Such polypeptides or polynucleotides could be part of a composition, and still be isolated in that such composition is not part of its natural environment.

Affinity techniques are particularly useful in the context of isolating HE4a polypeptides for use according to the methods of the present invention, and may include any method that exploits a specific binding interaction with a HE4a polypeptide to effect a separation. For example, because HE4a polypeptides may contain covalently attached oligosaccharide moieties, an affinity technique such as binding of a HE4a polypeptide to a suitable immobilized lectin under conditions that permit carbohydrate binding by the lectin may be a particularly useful affinity technique. Other useful affinity techniques include immunological techniques for isolating a HE4a polypeptide, which techniques rely on specific binding interaction between antibody combining sites for antigen and antigenic determinants present in the complexes. Immunological techniques include, but need not be limited to, immunoaffinity chromatography, immunoprecipitation, solid phase immunoadsorption or other immunoaffinity methods.

As described herein, the invention provides a fusion protein comprising a polypeptide fused to a HE4a. Such HE4a fusion proteins are encoded by nucleic acids that have the HE4a coding sequence fused in frame to an additional coding sequence to provide for expression of a HE4a polypeptide sequence fused to an additional functional or non-functional polypeptide sequence that permits, for example by way of illustration and not limitation, detection, isolation and/or purification of the HE4a fusion protein. Such 1-1E4a fusion proteins may permit detection, isolation and/or purification of the HE4a fusion protein by protein-protein affinity, metal affinity or charge affinity-based polypeptide purification, or by specific protease cleavage of a fusion protein containing a fusion sequence that is cleavable by a protease such that the HE4a polypeptide is separable from the fusion protein.

Thus, HE4a fusion proteins may comprise affinity tag polypeptide sequences, which refers to polypeptides or peptides added to HE4a to facilitate detection and isolation of the HE4a via a specific affinity interaction with a ligand. The ligand may be any molecule, receptor, counterreceptor, antibody or the like with which the affinity tag may interact through a specific binding interaction as provided herein. Such peptides include, for example, poly-His or the antigenic identification peptides described in U.S. Pat. No. 5,011,912 and in T. P. Hopp, B. Gallis and K. S. Prickett (1988) A short polypeptide marker sequence useful in protein identification and purification. Bio/Technology 6:1204-1210, or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson I A, Niman H L, Houghten R A, Cherenson A R, Connolly M L, Lerner R A. The structure of an antigenic determinant in a protein. Cell. 1984 July; 37(3):767-78).

HE4a fusion proteins may, in particularly embodiments and as described in greater detail below, further comprise immunoglobulin constant region polypeptides added to HE4a to facilitate detection, isolation and/or localization of HE4a. The immunoglobulin constant region polypeptide preferably is fused to the C-terminus of a HE4a polypeptide. According to non-limiting theory, inclusion of immunoglobulin (Ig) constant region domains in HE4a fusion proteins as provided herein may offer advantages, for example, those associated with the immunogenic/non-immunogenic properties of particular Ig regions when used in particular hosts (i.e., "self" vs. "non-self"), or those which facilitate isolation and/or detection of a fusion protein. These and other advantages of Ig fusion proteins will be appreciated by those familiar with the art. General preparation of fusion proteins comprising heterologous polypeptides fused to various portions of antibody-derived polypeptides (including the Fc domain) has been described, e.g., by Ashkenazi A, Marsters S A, Capon D J, Chamow S M, Figari I S, Pennica D, Goeddel D V, Palladino M A, Smith D H. Protection against endotoxic shock by a tumor necrosis factor receptor immunoadhesin. Proc Natl Acad Sci USA. 1991 Dec. 1; 88(23):10535-9 and Byrn et al. (Byrn R A, Mordenti J, Lucas C, Smith D, Marsters S A, Johnson J S, Cossum P, Chamow S M, Wurm F M, Gregory T, et al. Biological properties of a CD4 immunoadhesin. Nature. 1990 Apr. 12; 344(6267):667-70. A gene fusion encoding the HE4a:Fc fusion protein is inserted into an appropriate expression vector. In certain embodiments of the invention, HE4a:Fc fusion proteins may be allowed to assemble much like antibody molecules, whereupon interchain disulfide bonds form between Fe polypeptides, yielding dimeric HE4a fusion proteins.

HE4a fusion proteins having specific binding affinities for pre-selected antigens by virtue of fusion polypeptides comprising immunoglobulin V-region domains encoded by DNA sequences linked in-frame to sequences encoding HE4a are also within the scope of the invention, including variants and fragments thereof as provided herein. General strategies for the construction of fusion proteins having immunoglobulin V-region fusion polypeptides are disclosed, for example, in EP 0318554; U.S. Pat. No. 5,132,405; U.S. Pat. No. 5,091,513; and U.S. Pat. No. 5,476,786.

The nucleic acid of the present invention may also encode a fusion protein comprising a HE4a polypeptide fused to other polypeptides having desirable affinity properties, for example an enzyme such as glutathione-S-transferase. As another example, HE4a fusion proteins may also comprise a HE4a polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypeptides for construction of HE4a fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049; U.S. Pat. No. 5,272,254 and elsewhere, and avidin fusion proteins (see, e.g., EP 511,747). As provided herein and in the cited references, HE4a polypeptide sequences may be fused to fusion polypeptide sequences that may be full-length fusion polypeptides and that may alternatively be variants or fragments thereof.

The present invention also contemplates HE4a fusion proteins that contain polypeptide sequences that direct the fusion protein to the cell nucleus, to reside in the lumen of the endoplasmic reticulum (ER), to be secreted from a cell via the classical ER-Golgi secretory pathway (see, e.g., von Heijne, G. (1990) The Signal Peptide. J. Membr. Biol. 115, 195-201, to be incorporated into the plasma membrane, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar (see by way of example, Rothman J E. Mechanisms of intracellular protein transport. Nature. 1994 Nov. 3; 372(6501):55-63, Advani R J, Bae H R, Bock J B, Chao D S, Doting Y C, Prekeris R, Yoo J S, Scheller R H. Seven novel mammalian SNARE proteins localize to distinct membrane compartments. J Biol Chem. 1998). Accordingly, these and related embodiments are encompassed by the instant compositions and methods directed to targeting a polypeptide of interest to a predefined intracellular, membrane or extracellular localization.

The present invention also relates to vectors and to constructs that include nucleic acids of the present invention, and in particular to "recombinant expression constructs" that include any nucleic acids encoding HE4a polypeptides according to the invention as provided above; to host cells which are genetically engineered with vectors and/or constructs of the invention and to the production of HE4a polypeptides and fusion proteins of the invention, or fragments or variants thereof, by recombinant techniques. HE4a proteins can be expressed in mammalian cells, yeast, bacteria, or other cells under the control of appropriate promoters. Cell-free translation systems can also be employed to produce such proteins using RNAs derived from the DNA constructs of the present invention.

Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as they are replicable and viable in the host.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as provided herein may be included in any one of a variety of expression vector constructs as a recombinant expression construct for expressing a HE4a polypeptide. Such vectors and constructs include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Any one or more of a number of standard techniques known can be utilized.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a HE4a polypeptide is described herein.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pal III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+en-vAm12, and DAN cell lines as described in Miller, *Human Gene Therapy*, 1:5-14 (1990), which is incorporated herein by reference in its entirety. The vector may transduce the packaging cells through any means known in the art. Such means include, but are not limited to, electroporation, the use of liposomes, and calcium phosphate precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the HE4a polypeptides or fusion proteins. Such retroviral vector particles then may be employed, to transduce eukaryotic cells, either in vitro or in vivo. The transduced eukaryotic cells will express the nucleic acid sequence(s) encoding the HE4a polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, bronchial epithelial cells and various other culture-adapted cell lines.

As another example of an embodiment of the invention in which a viral vector is used to prepare the recombinant HE4a expression construct, in one preferred embodiment, host cells transduced by a recombinant viral construct directing the expression of HE4a polypeptides or fusion proteins may produce viral particles containing expressed HE4a polypeptides or fusion proteins that are derived from portions of a host cell membrane incorporated by the viral particles during viral budding. In another preferred embodiment, HE4a encoding nucleic acid sequences are cloned into a baculovirus shuttle vector, which is then recombined with a baculovirus to generate a recombinant baculovirus expression construct that is used to infect, for example, SD host cells, as described in *Baculovirus Expression Protocols, Methods in Molecular Biology* Vol. 39, C. D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology*, 2nd Ed., Ausubel et al., eds., John Wiley & Sons, New York, N.Y., 1992, pages 16-32 to 1648.

In another aspect, the present invention relates to host cells containing the above described recombinant HE4a expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding HE4a polypeptides or HE4a fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* 52 and *Spodoptera* Sj9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. The invention is therefore directed in part to a method of producing a recombinant HE4a polypeptide, by culturing a host cell comprising a recombinant expression construct that comprises at least one promoter operably linked to a nucleic acid sequence encoding a HE4a. In certain embodiments, the promoter may be a regulated promoter as provided herein, for example a tetracylcine-repressible promoter. In certain embodiments the recombinant expression construct is a recombinant viral expression construct as provided herein. Examples of mammalian expression systems include the COS-7 lines of monkey kidney fibroblasts, described by Gluzman Y. SV40-transformed simian cells support the replication of early SV40 mutants. Cell. 1981 January; 23(1):175-82 and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of MRA expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis, L. G., Dibner, M. D. and Battey, J. F.: Basic Methods in Molecular Biology. Elsevier, New York, 1986).

The expressed recombinant HE4a antigen polypeptides (or HE4a polypeptides), or fusion proteins derived therefrom, may be useful as immunogens in the form of intact host cells; intact organdies such as cell membranes, intracellular vesicles or other cellular organelles; or disrupted cell preparations including but not limited to cell homogenates or lysates, uni- and multilamellar membrane vesicles or other preparations. Alternatively, expressed recombinant antigen polypeptides or fusion proteins can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography including immunoaffinity chromatography, hydroxylapatite chromatography and lectin chromatography. Protein refolding steps can be used, as necessary, in completing configuration of the mature protein. Finally, high performance liquid chromatography (HPLC) can be employed for final purification steps. Expressed recombinant HE4a antigen polypeptides (or HE4a polypeptides) or fusion proteins may also be useful as target antigens in any of a number of assay configurations for routine antibody screening, which can be readily performed by those having ordinary skill in the art.

The HE4a antigen polypeptide (or HE4a polypeptide) that is an immunogen for the production of a specific antibody to be used in the method of the present invention may thus be a naturally purified product, or a product of chemical synthetic procedures, or produced by recombinant techniques from a prokaryotic or, preferably, a eukaryotic host. Depending upon the host employed in a recombinant production procedure, the polypeptides of the present invention may be glycosylated or otherwise posttranslationally modified as known in the art and as provided herein.

The subject matter of this disclosure is now described with reference to the following Examples. These Examples are provided for the purpose of illustration only, and the subject matter is not limited to these Examples, but rather encompasses all variations that are evident as a result of the teaching provided herein.

EXAMPLES

Prior to the experiments described herein, there was no published protocol that allows for optimal measurement of N-WFDC domain of HE4a in a sample from a subject using an immunocytochemistry (IHC) assay format. Aspects and embodiments of the instant disclosure stem from the unexpected discovery that 12A2 and 14E2 monoclonal antibodies have surprising and unexpected utility and efficacy when used concurrently or in combination for assessing presence of full length HE4/HE4a.

In the experiments described herein, several factors were discovered that allowed for the unexpected enhanced/potentiated efficacy. For example, it was discovered that by using the 12A2/14E2 antibodies in certain combinations with 2H513D8, a more specific full-length HE4 recognition and binding profiles can be obtained. In addition, it was also discovered that during the analysis of HE4 in test ovarian cancer samples (including full length HE4 samples), the use of 12A2 or 14E2 antibodies in combination with 2H5 or 3D8, in an exemplary diagnostic assay, including IHC, the resultant corresponding clinical data and/or disease correlation exhibited an unexpected reduced background and/or surprisingly improved resolution in the assessment of HE4 profiles.

By way of example, recombinant HE4 fusion proteins for the immunization in production of HE4 monoclonal Ab were developed.

Example 1

Production of recombinant full length HE4ahIg/mIg, HE4a-V4HIg/mIg and HE4a-V2-hIg/mIg fusion proteins: Amplification of HE4a (WFDC2) cDNA from a Highthroughput HE4a cDNA Clone toward Construction of a Fusion Construct.

The HE4a (WDFC2) gene was combined with genes encoding IgG to construct fusion proteins to immunize mice and obtain Monoclonal antibodies (MAbs). The mice were immunized against fusion proteins with a mouse Ig tail, and the hybridomas were screened against fusion proteins with a human Ig tail. Subsequently, a double determinant (Sandwich) ELISA was developed.

The mRNA sequence for HE4a as originally published by Kirchoff et al. (15, 22) and deposited in GenBank (accession no. X63 187) provided the basis for oligonucleotide primer design to clone cDNA that encodes HE4a. To clone HE4a cDNA, RNA was prepared from ovarian tumors, normal epididymis and from several ovarian tumor cell lines, including 4007 and OVCAR3 (24), using TRIzol (Life Technologies, Inc., Gaithersburg, Md.) according to the manufacturer's instructions. cDNA was prepared using 1-3 µg of RNA, random hexamers, and Superscript II Reverse Transcriptase (Life Technologies, Inc.) according to the manufacturer's directions. HE4a cDNA was PCR amplified from the random primed cDNA using standard conditions. PCR products of the expected size for the full-length HE4a were obtained and then cloned. Sequence analysis identified differences compared to the sequence of Kirchoff et al and the corrected sequence for HE4a, deposited in GenBank (accession no. AY212888) was used to construct the fusion proteins. A sequence verified cDNA fragment containing the full-length HE4a gene was cloned into p SPORT and this plasmid DNA was used as PCR template for construction of the fusion clones.

Fusion proteins were constructed that incorporated the complete HE4a gene product fused to the human or mouse IgG Fc domain. Primers were designed that encoded appropriate restriction sites for cloning and created the necessary in-frame fusions of protein domains for the final construct. The 5' primer (5 GTTGTTAAGC TTGCCGCCAT GCCTGCTTGT CGCCTAGGC-3' (SEQ ID NO: 2;)) included a HindIII site, a Kozak sequence to improve expression adjacent to the first ATG, and a portion of the HE4a leader peptide based on the HE4a sequence. The 3' primer (5' GTTGTTGGAT CCGAAATTGG GAGTGACACA GGA-CAC-3' (SEQ ID NO: 4;)) included an in-frame BamHI site for fusion to the human/mouse-Ig tail cDNA, with the 3' end of the HE4a coding sequence truncated just before the STOP codon. PCR amplification reactions were performed according to manufacturer's instructions (ExTaq; Takara Bio, Inc., Otsu, Shiga, Japan) using 100 ng of HE4a/pSPORT plasmid as a template and 30 cycles of amplification (1 min at 94° C., 1 min at 55° C., and 30 s at 72° C.). PCR products of the expected size (400 bp) for the full-length HE4a were obtained and then purified using the QIAQUICK PCR Purification Kit (QIAGEN, Valencia, Calif.). The purified PCR fragments were restriction digested, purified using the QIAEX II Gel Extraction Kit (Qiagen QIAGEN), and ligated in fusion with mouse IgG2a Fc (mIgG2a) and human IgG1 Fc (hIgG1) into the mammalian expression vector pD18, a derivative of pCDNA 3 as described previously. FIG. 1 shows schematically how the FL HE4a-mIgG2a and FL HE4a-hIgG1 cDNA constructs were inserted as a HindIII-XbaI fragment into the multiple cloning site of pD18.

Ligation products were transformed into DH5α bacterial cells, and transformants were screened for the presence of FL HE4a-mIgG2a and FL HE4a-hIgG1 fusion gene inserts and verified by sequence analysis. In addition, protein expression was confirmed using plasmid DNA from these isolates to transiently transfect COST cells by the DEAE-Dextran technique as described. Culture supernatants were harvested after 72 h and screened by immunoprecipitation with protein Agarose (Repligen, Cambridge, Mass.), reducing SDS-PAGE electrophoresis, and Western blotting. Western blots were probed using a goat antihuman IgG horseradish peroxidase conjugate (Caltag, Burlingame, Calif.) at 1:5000, followed by enhanced chemiluminescence development (Amersham, Little Chalfont, United Kingdom). Plasmid DNA with sequence verified HE4a gene in fusion with the human IgG1 Fc tail (pD18-HE4a-hIgG plasmid) was used as template for amplification and cloning of the HE4a splice variants HE4a-V4 and HE4a-V2 described in the publication of Bingle et al (Bingle L., Singleton V., Bingle C. D. The putative ovarian tumour marker gene HE4 (WFDC2), is expressed in normal tissues and undergoes complex alternative splicing to yield multiple protein isoforms. Oncogene, 21: 2768-2773, 2002). The HE4a-V4 and HE4a-V2 splice variants were cloned in fusion with mouse and human IgG Fe as described for the full-length HE4a above. The nucleotide primers used for amplification are listed below.

```
For HE4a-V4:
Forward primer:
                                            (SEQ ID NO: 21)
5'-GTTGTTACCGGTGCAGCAGAGAAGACTGGCGTGTGCCCC-3'

Reverse primer:
5'-AATCTCCCAGAGCCTCCGTGTCTTTAGGTGCCAGTGGAACAGTGCA

TTGGGCAGAGAGCA-3'

For HE4a-V2:
Forward primer:
                                            (SEQ ID NO: 25)
5'-GTTGTTACCGGTGCAAAGGAGGGTTCCTGCCCCCAG-3'

Reverse primer:
                                            (SEQ ID NO: 27)
5'-GTTGTTGGATCCGAAATTGGGAGTGACACAGGA-3'
```

Production of HE4aIg Fusion Proteins.

Stable cell lines of the full length HE4a-mIgG2a and HE4a-hIgG1 cDNA constructs and the corresponding constructs with the HE4a-V4 and HE4a-V2 spice variants were established. CHO-DG44 cells were used to construct stable lines expressing high levels of the fusion proteins of interest. Stable CHO lines were created by high copy electroporation of the plasmid constructs and selection of methotrexate-resistant clones by limiting dilution in Excell 302 CHO media (JRH Biosciences, Denver, Pa.) containing recombinant insulin (Life Technologies, Inc.), sodium pyruvate (Invitrogen Corp., Carlsbad, Calif.), L-glutamine (Invitrogen Corp.), 2× nonessential amino acids (Invitrogen Corp.), and 100 nM methotrexate (Sigma, St. Louis, Mo.). Culture supernatants from resistant clones were then assayed by IgG sandwich ELISA to screen for high producing lines. Spent supernatants were harvested from large-scale cultures, and IgG fusion protein was purified by protein A affinity chromatography, after which the fusion proteins were checked by Western blotting (data not shown). The HE4a-hIgG1 fusion protein migrated at an apparent molecular weight of Mw48,000 on reduced gels or Western blots, larger than the Mr 36,000 expected based on the predicted amino acid sequence, suggesting that the molecule was glycosylated. Stable transfectants were used to produce enough protein for immunization of BALB/c mice.

By way of example, hybridomas and monoclonal antibodies specific for HE4a N-WFDC domain were developed.

Example 2

Establishment of Hybridomas and Monoclonal Antibodies Specific for HE4a N-WFDC Domain BALB/c mice were immunized biweekly, 5 times, with HE4a-V4 mIgG and a sixth time with FL HE4a. Three days after the last immunization the mice were sacrificed and hybridomas were made as previously described for mesothelin. Hybridoma supernatants were screened on HE4a-V4 hIgG, and hybridomas 12A2 and 14E2 were selected based on their reactivity with HE4a-V4 hIgG. The hybridomas were cloned twice according to standard procedures and the selected clones were used for production of HE4a N-WFDC MAb. Monoclonal antibodies were produced by in vitro cultivation of the hybridoma clones by inoculation of $10^4$ cells/mL in DMEM, 5% Fetal Calf Serum in roller bottles and allowed to grow for 10-14 days. The monoclonal antibodies were then purified from the culture medium by Protein A affinity chromatography according to the manufacturers recommendation.

Example 3. Characterization of Binding Specificity of the mAb Against ME4a N-WFDC Domain 3.1 Reactivity with hIgG HE4a Fusion Proteins The specificity of the 12A2 and 14E2 MAb were then tested in ELISA on FL HE4a, HE4a-V4 and HE4a-V2 hIgG fusion proteins. The 12A2 and 14E2 MAb were coated in wells of microtiter plates by incubation of the MAb's (10 µg/mL) in carbonate-bicarbonate buffer (C-3041; Sigma). After removal of the supernatant, the wells were blocked for 2 hr at room temperature with 200 µl/well GSC blocking buffer (Genetic Systems, Seattle). This was followed by four washes, 200 µl/well, with PBS containing 0.1% Tween.

The MAb coated wells were then incubated with 100 µl/well of FL HE4a, HE4a-V4 and HE4a V2 for 2 h. Bound HIgG HE4a fusion protein was then detected by incubation with HRP conjugated Anti-hIgG1 and determination of 0D450 nm.

Figure 2:
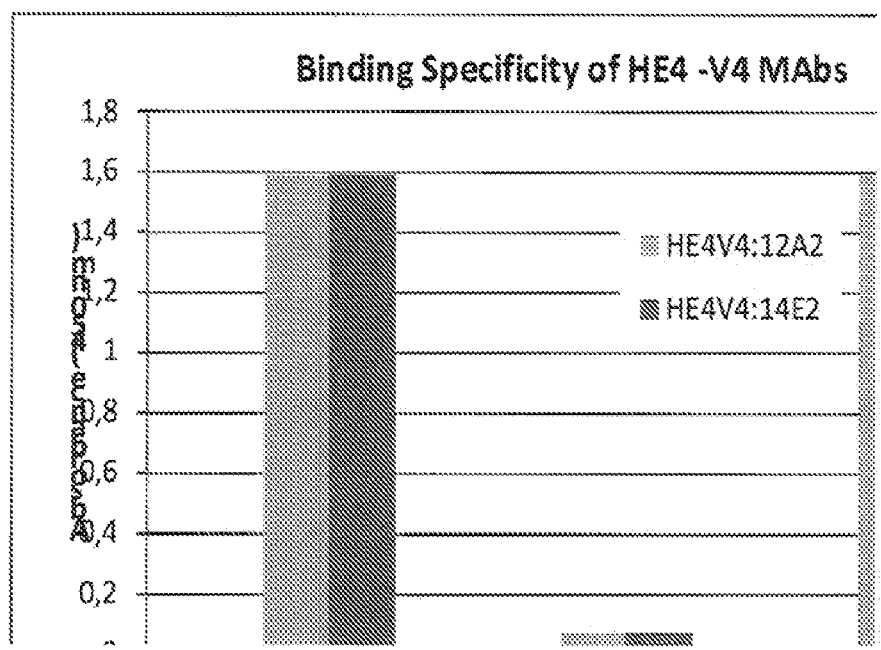
FIG. 2 illustrates some binding specificities of the monoclonal antibody embodiments (12A2 and 14E2 antibodies) to the full length HE4a, HE4a-V4 and HE4a-V2 domains of HE4a. In this example, the MAbs 12A2 and 14E2 bound to HE4a-V4 variant and to full length HE4a but not to the HE4a-V2 domain. Indicating that the 12A2 and 14E2 MAb's bound to the HE4a N-WFDC domain.

The 12A2 and 14E2 MAb reacted with Full length HE4a and HE-V4 indicating that they were specific for the HE4a N-WFDC domain, FIG. 2.

Figure 3:
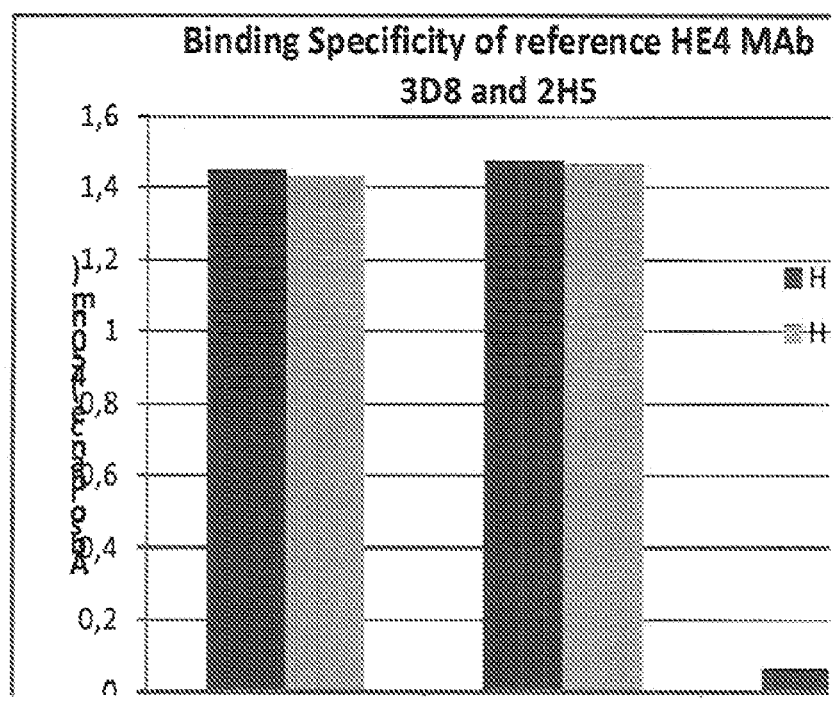
FIG. 3 depicts the binding specificities of the reference monoclonal antibodies (2H5 and 3D8 antibodies, deposited with the ECACC as Patent Deposit Nos. 13070301 and 13070304, respectively) to fusion proteins. In this example, the reference MAbs bind to the HE4a-V2 domain and to full length HE4a but not to the HE4a-V4 domain, indicating that they recognized epitopes in the HE4a C-WFDC domain.

The specificity of the 3D8 and 2115 MAb were also tested as reference MAb's using the same methodology, FIG. 3.

3.2 Reactivity with HE4a Domains Displayed as Phage Fusion Proteins

The specificity of the 12A2 and 14E2 MAb for the HE4a N-WFDC domain was further confirmed by testing the reactivity towards HE4a N-WFDC domain and HE4a C-WFDC domain expressed as fusion proteins with phage coat protein pVIII in a phage ELISA.

cDNA, prepared from mRNA isolated from OvCar-3 cells, served as template for PCR amplification of the gene parts coding for the C- and N-terminal WFDC regions for cloning in the phage display vector f88-4. PCR primer pairs, listed in Table 2, were constructed for amplification of the coding regions of amino acid residues 31-75 (N-WFDC) and 76-124 (C-WFDC) respectively. In the 5'-ends were restriction sites for HindIII and PstI inserted for cloning in fusion with the pVIII signal peptide and the pVIII mature coat protein.

TABLE 2

PCR primers used for amplification of HE4a N- and C- WFDC

| Primer | SEQ ID NO: | Sequence | WFDC |
|---|---|---|---|
| W1F | 29 | 5-TGCTAAGCTTTGCCGAGAAGACTGGCGTG TGCCC-3' | N-WFDC |
| W1R | 31 | 5'-CCTTCTGCAGGATCATTGGGCAGAGAGC AG-3' | N-WFDC |
| W2F | 33 | 5'-TGCTAAGCTTTGCCAAGGAGGGTTCCTG CCCCCA-3' | C-WFDC |
| W2R | 35 | 5'-CCTTCTGCAGGGAAATTGGGAGTGACAC AGGA-3' | C-WFDC |

The WFDC regions were separately amplified from 0.5 µl of cDNA in a reaction mixture containing 1 µM of each forward and reverse primer, 75 mM Tris-HCl (pH 8.8 at 25° C.), 20 mM $(NH_4)_2SO_4$, 0.1% (v/v) Tween 20, 2 mM $MgCl_2$, 0.02 u/µl Taq-polymerase (Abgene, Surrey, UK) and 0.1 mM of each deoxynucleotide in a final volume of 25 μl with the following temperature cycle repeated 30 times: 30 seconds incubations at 95° C., 50° C. and 72° C.

PCR products and 188-4, digested with HindIII and PstI, were ligated together and transfected into E. coli JM109 where after clones were selected on LB plates with tetracycline. Two clones of each construct were amplified in E. coli JM109 and double-stranded DNA was prepared for DNA sequencing. DNA sequencing was performed using the Big dye terminator v1.1 cycle sequencing kit and a f88-4 vector specific primer. Sequencing reactions were sent to CyberGene AB (Huddinge, Sweden) for analysis. Sequence raw data was analyzed using the free software Chromas version 1.45 (Technelysium Pty Ltd., Australia). Nucleotide sequencing verified insertion in frame with the leader peptide and the mature phage coat protein pVIII. The HE4a inserts demonstrated identity to the HE4a sequence (accession number AY212888), FIG. 4.

Phage ELISA

Figure 5:
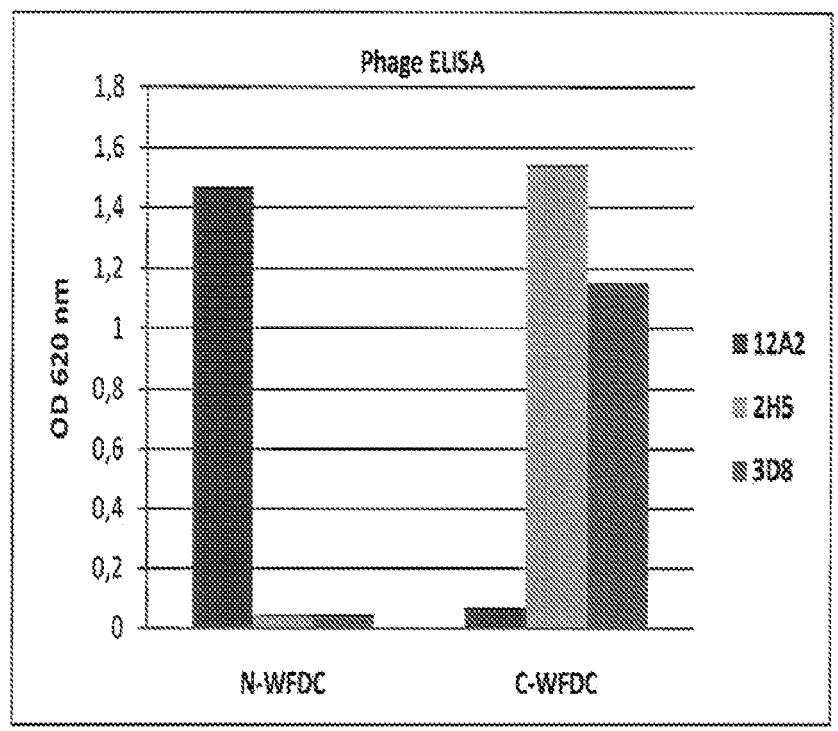
FIG. 5 illustrates the binding interaction of the exemplary monoclonal antibodies (12A2) to N-WFDC and C-WFDC. In this example, the binding specificity of 12A2 is demonstrated using a phage ELISA format wherein the MAb reacted only with the HE4a N-WFDC phage pVIII fusion protein.

Sequence verified phage clones were amplified, purified, concentrated with PEG/NaCl and were diluted in 1% BSA in PBS for use as antigen in the phage ELISA assay. MAb 3D8 and 2H5, diluted to 1 μg/ml in 1% BSA in PBS, and MAb 12A2, in 100 μl clone medium, were immobilized in wells (100 μl/well) coated with goat anti mouse IgG (Jackson Immuno Research). The plates were sealed and stored over night at room temperature. Wells coated with the HE4a MAbs were washed three times and phage particles in a volume of 100 μl/well were added. After two hours incubation, wells were washed and a rabbit anti-M13 antibody (established in-house) was added. After incubation and washing, a HRP labelled swine anti rabbit antibody (Dako) was added. After the final wash TMB substrate was added and the plate was measured at 620 nm after 5 minute incubation, FIG. 5.

The Phage ELISA studies using the N-WFDC and C-WFDC domains displayed as fusion proteins with phage protein pVIII and the reactivity towards HE4a-V2, HE4a-V4 and FL HE4a hIgG1 fusion proteins confirmed that the 12A2 and 14E2 MAb were specific for HE4a N-WFDC domain.

3.3 Characterisation of Epitopes Recognized by 12A2 and 14E2 MAb's

The type of epitopes, i.e. linear or conformational dependent epitopes, recognized by the 12A2 and 14E2 MAb were determined by testing the reactivity of the antibodies towards denatured and reduced HE4a antigens. Spent medium from the stable cell line producing full-length HE4a-hIgG1, undiluted and diluted five times, were denaturated at 70° C. and separated with SDS-PAGE under reducing conditions. The proteins were blotted onto a PVDF membrane according to standard techniques. After incubating the membrane with the primary HE4a antibodies bound antibodies were traced by a HRP swine anti mouse antibody (Dako). The HRP antibody was detected by chemiluminescence using the Amersham™ ECL™ detection systems.

Figure 6:
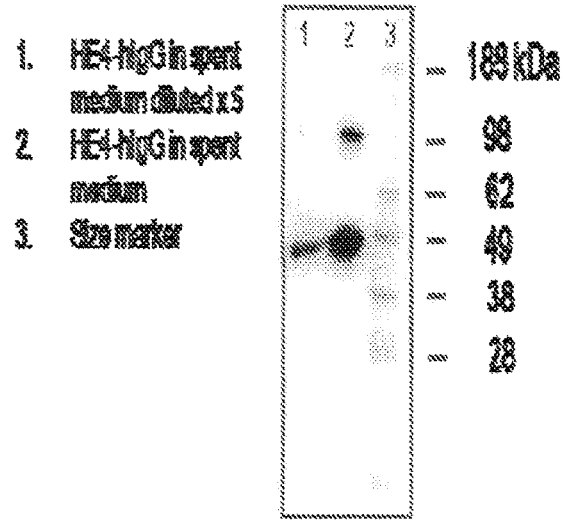
FIG. 6 depicts the reactivity of 14E2 MAb with denatured and reduced HE4a-hIg fusion protein. The binding to denatured and reduced HE4a-hIg fusion protein indicated that the 14E2 MAb recognized a linear epitope of the HE4a protein.

MAb 12A2 demonstrated no reactivity against the denaturated and reduced HE4a antigen (data not shown) indicating that the antibody recognized a conformational dependent epitope. MAb 14E2 on the other hand demonstrated specific staining to a band of approximately 48 kDa that is the expected size of the glycosylated HE4a-hIgG1 fusion molecule. In the lane with the higher antigen concentration a band of about twice the size was observed. This band most likely represents a dimer of the antigen in which the disulfide bounds in the Fc part have not been completely broken. The western blot data indicate that MAb 14E2 recognized a linear epitope, FIG. 6.

3.4 Independent Epitopes of the Established HE4 N-WFDC Specific Antibodies

The difference in reactivity of 12A2 and 14E2 MAb towards denatured and reduced HE4a antigen indicate that the two antibodies recognized two independent epitopes of HE4a N-WFDC domain.

Figure 7:
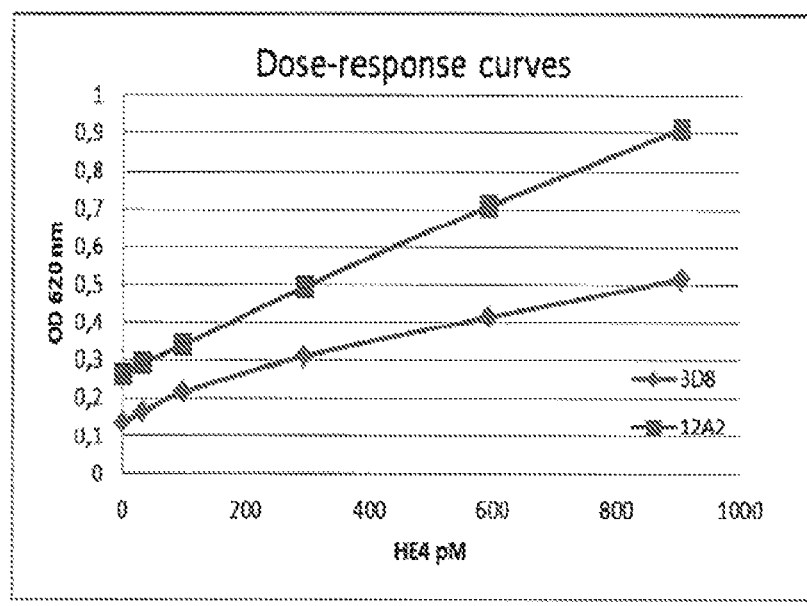
FIG. 7 shows a dose-response curve of sandwich immunoassays using 14E2 as capture MAb and 3D8 or 12A2 MAB as detecting MAb. The results for the combination of 14E2 and 12A2 MAb indicated that they are able to bind simultaneously and thus detect independent epitopes of HE4a N-WFDC domain.

The recognition of independent epitopes in the HE4a N-WFDC domain by the 12A2 and 14E2 MAb were further confirmed by combining 12A2 and 14E2 MAb in a sandwich immunoassay. MAb 14E2 was used as capture MAb in combination with HRP labeled MAb 12A2 as detecting antibody and determination of the dose response curve with HE4a antigen. MAb 14E2 in concentrated hybridoma medium was captured in micro wells coated with a goat anti mouse antibody (Jackson ImmunoResearch Lab). After washing, 25 μl of HE4a antigen (0-900 pM) from the HE4a EIA kit (Fujirebio Diagnostics Inc) was added and thereafter the HRP-labeled 12A2 MAb was added. As a control experiment a parallel run was performed with the 14E2 MAb solid phase and HRP labeled tracer MAb 3D8, used in HE4a EIA. MAb 3D8 is known to target the C-terminal WAP region and therefore should form a sandwich EIA pair with MAb 14E2. After incubation and washing steps, TMB substrate was added and the absorbance was analyzed at 620 nm after a 30 minutes incubation step. Both MAb 3D8 and 12A2 demonstrated a dose-response curve with MAb 14E2, FIG. 7.

The positive dose response curve of the sandwich immunoassay of 12A2 MAb and 14E2 MAb in addition to their different reactivity with reduced HE4a antigen proved that MAb 14E2 and MAb 12A2 recognized independent epitopes specific for the HE4a N-WFDC domain.

Immunoassays specific for full length HE4a were also developed.

Example 4

Establishment of Immunoassays Specific for Full Length HE4a

Assays specific for full length HE4a (FL HE4a) were designed by using antibodies specific for N-WFDC and C-WFDC domain.

In one aspect of the invention the antibodies specific for HE4a N-WFDC domain was combined with antibodies specific for the HE4a C-WFDC domain to allow the design of an immunoassay specific for full length HE4a, while failing to detect either the HE4a N-WFDC, HE4a C-WFDC domains or the HE4a-V4 or HE4a-V2 variants.

Figure 8:
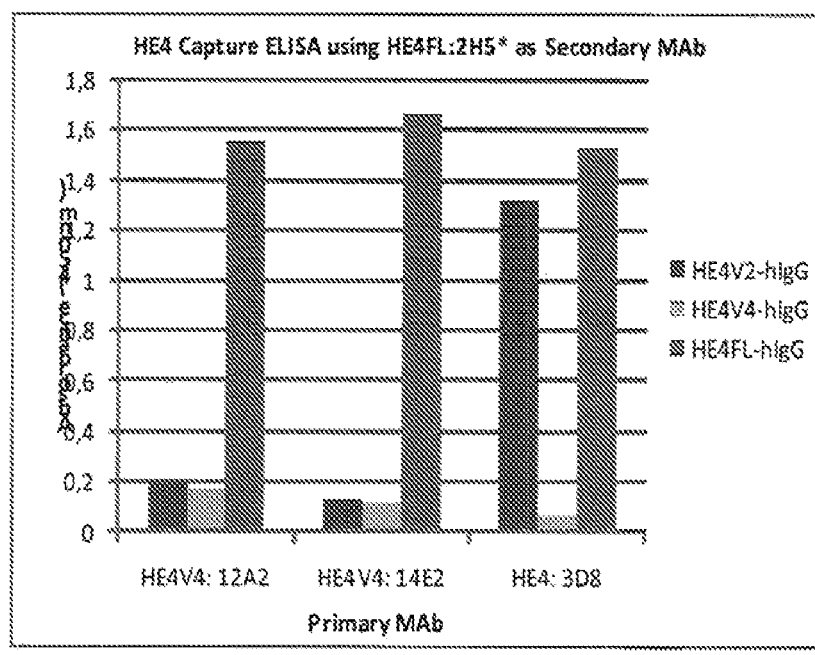
FIG. 8 illustrates some example sandwich immunoassays and the binding of the 12A2 and 14E2 MAb's in combination with 2H5 MAb. In this example, MAb 12A2 and 14E2 reacted only with full length HE4a, while the MAb combination 3D8 and 2H5 reacted with both FL HE4a and HE4a-V2 variant. The result further support the evidences that that 12A2 and 14E2 MAb recognize epitope exposed in HE4a N-WFDC domain.

In an initial experiment the 12A2 MAb and 14E2MAb according to the present invention and 3D8 MAb reactive towards the HE4a C-WFDC domain (Hellström et al; The HE4 (WFDC2) Protein Is a Biomarker for Ovarian Carcinoma; *Cancer Res* Jul. 1, 2003 63; 3695) were used as capture antibody in a sandwich assay using the 2H5 MAb reactive towards the HE4a C-WFDC domain as detecting antibody. In the sandwich assays the different capture MAbs were immobilized in microtiter wells using similar procedure as described in Example 2 and incubated with hIgFc fusion proteins of FL HE4a, HE4a-V4 and HE4a-V2 domain. The bound HE4a proteins were then detected by incubation with biotinylated 2H5 MAb followed by incubation with Streptavidin HRP and determination of OD 450 nm after incubation with OPD HRP substrate. The sandwich assay demonstrated that the combination of 12A2 MAb or 14E2 MAb in combination with 2H5 MAb detected only the FL HE4a fusion protein, while the combination of 3D8 MAb and 2H5 MAb detected both FL HE4a and HE4a.V2 variant, FIG. 8.

In the preferred configuration for design of an immunoassay specific for FL HE4a the 2H5 MAb was used as catching antibody and 12A2 MAb as detecting antibody. 2H5 MAb was biotinylated with Biotin-NHRS caproate ester, Sigma Chemical Co, US, using standard procedures, and used as catching antibody. 12A2 MAb were conjugated with HRP according to a modification of the Nakone procedure. The biotinylated 2H5 MAb and HRP conjugated 12A2 MAb were used in one-step EIA according to the following protocol.

Assay Procedure:

Add 25 µL of FL HE4a-hIgG recombinant antigen (0-1000 pM in PBS, 60 g/L BSA, pH 7.2)+100 µL of Biotin 2H5 MAb, 1 µg/mL and HRP12A2 MAb, 1 µg/mL in Assay Buffer in Streptavidin coated microtiter plates, Kaivogen Oy, Turku, Finland.

2. Incubate for 1 h±10 min with shaking
3. Wash 6 times with 5 mM Tris buffer, 0.05% Tween 40, pH 7.75.
4. Add 100 µL TMB, Neogen, US.
5. Incubate 30 min±5 min
6. Determine OD 620 nm in an ELISA reader.

Figure 9:
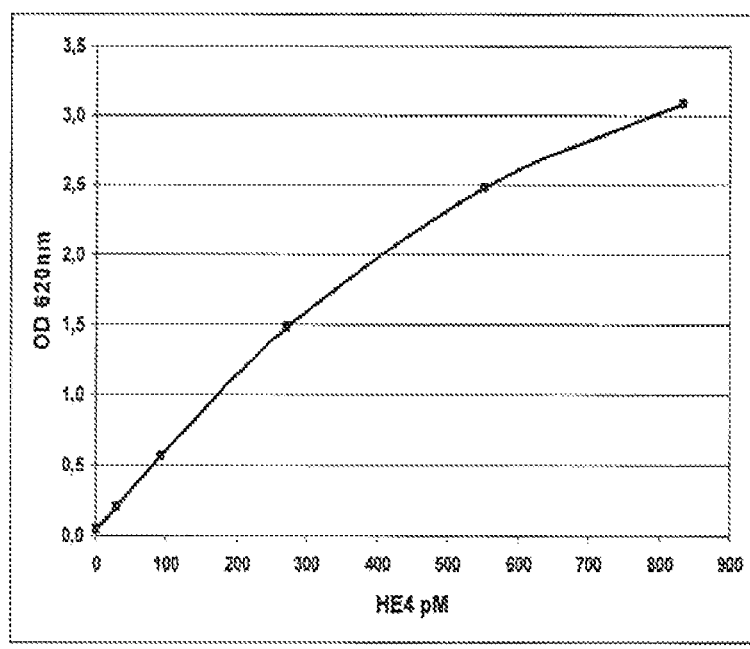
FIG. 9 shows a dose-response curve of full length HE4a EIA. This assay was based on 2H5 MAb as capture antibody and HRP conjugated 12A2 MAb as the detecting MAb. The procedure was performed as described in Example 3.

An example of the dose-response curve using HE4a-hIgG diluted in PBS, 60 g/L BSA for the assay is shown in FIG. 9. The sensitivity of the assay was <5 pM, which was significantly lower than what is found in healthy subjects. Thus the assay would be suitable for determination of FL HE4a in healthy subjects and in individuals with known or suspected ovarian cancer.

The purpose of this study is to assess the suitability of the new 12A2 MAb by evaluating their abilities in assessing the presence of full length HE4 in an exemplary assay format.

Example 5

Diagnosis of Ovarian Cancer Using Immunoassays Specific for Full Length HE4a

In one aspect of the disclosure antibodies were used to design immunoassays for serological diagnosis of ovarian cancer. The immunoassay for FL HE4a using 2H5 MAb in combination with 12A2 MAb as described in Example 3 was used to determine concentrations of full length HE4a in serum samples from healthy individuals, patients with benign gynecological disease and patients with ovarian cancer.

Figure 10:
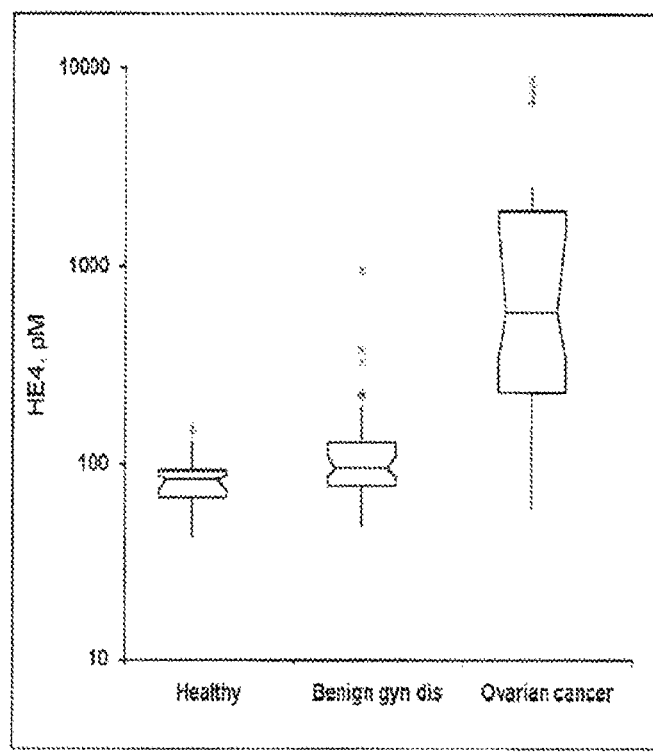
FIG. 10 depicts HE4a levels in healthy subjects, patients with benign gynecological diseases and ovarian cancer determined in the FL HE4a EIA as described in Example 3.

The levels of FL HE4a were significantly higher in patients with ovarian cancer (p<0.001) compared to patients with benign gynecological disease or healthy subjects, Table 3, FIG. 10.

TABLE 3

HE4a levels in healthy subjects and individuals with benign gynecological disease and patients with ovarian cancer.

|  | n | HE4A pM Mean | 95% Cl | SE | SD |
|---|---|---|---|---|---|
| Healthy | 50 | 84 | 77 to 91 | 3.4 | 24.4 |
| Benign gyn dis | 82 | 122 | 98 to 146 | 11.9 | 108.5 |
| Ovarian cancer | 25 | 2967 | 319 to 5614 | 1282.8 | 6413.8 |

The purpose of this study is to assess the suitability of the new 12A2 MAb/full length HE4 assay format by evaluating their abilities in determining and monitoring the course of ovarian cancer.

Example 6

Monitoring the Course of Disease in Ovarian Cancer by Determination of FL HE4a

In another aspect of the invention the immunoassays for determination of FL HE4a according to Example 3 were used to follow the clinical course of disease in patients with diagnosed ovarian cancer.

Figure 11:
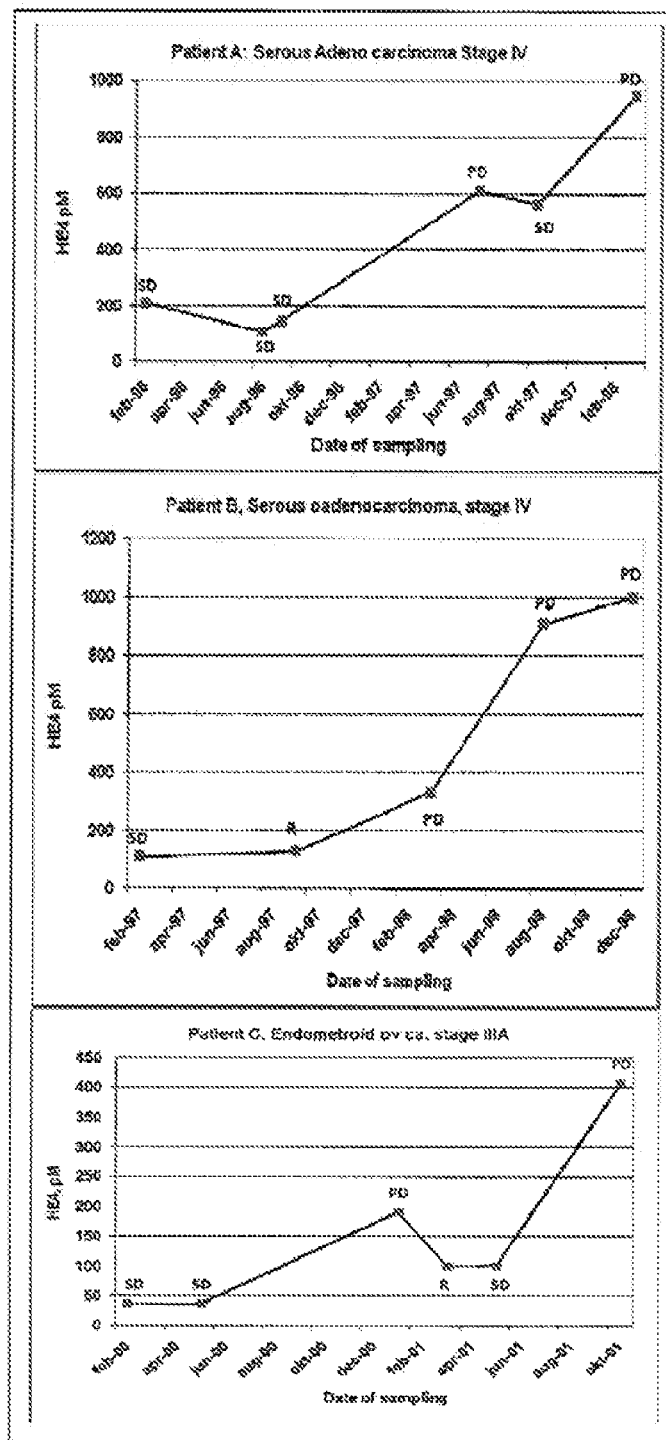
FIG. 11 illustrates an exemplary full length HE4a immunoassay for monitoring clinical course of ovarian cancer. (SD=Stable disease; R=Responding; PD=Progressive disease). In this Example the full length HE4a demonstrated that full length HE4a would be useful to follow the clinical course of disease of patients with diagnosed ovarian cancer.

FL HE4a levels in three patients with ovarian cancer are shown during the clinical course of the disease in FIG. 11. The FL HE4a levels followed the clinical course of disease and would be suitable to full the effect of therapy of ovarian cancer as well as detection of recurrent disease.

By way of example, the purpose of this study is to assess the suitability of the new 12A2 MAb/full length HE4 assay format in determining HE4 in tissue samples.

Example 7

Diagnosis of Ovarian Cancer by Determination of HE4a in Tissue Sections

In an additional aspect of the invention a method for diagnosis of ovarian cancer is provided by incubating the antibodies specific for the N-WFDC domain of HE4a with tissues or cells obtained from patients with suspected ovarian cancer and determination of binding of the antibodies to the tissue or cells.

Figure 12:
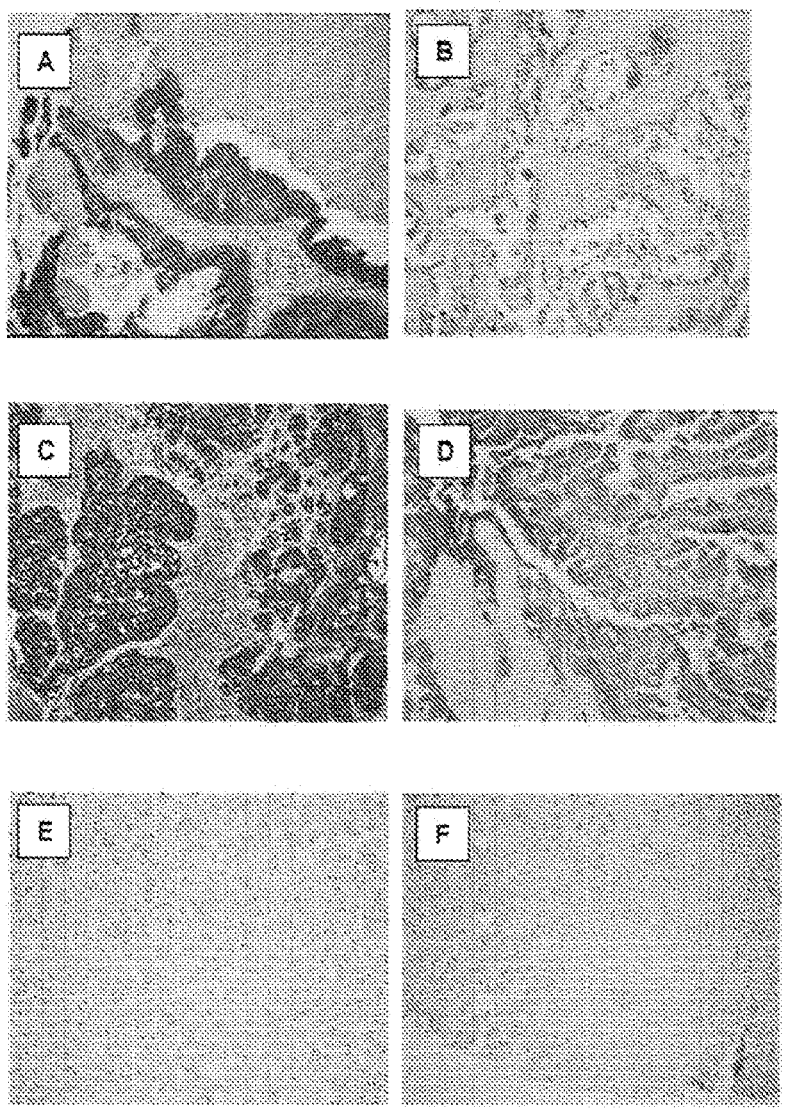
FIG. 12. Illustrates IHC of benign and malignant ovarian tissues using exemplary MAb specific for HE4a N-WFDC domain. In this example, the exemplary 12A2 MAb bound strongly to cancer cells in ovarian cancer, but did not bind to cells in benign tumors. A: Serous adenocarcinoma; B: Serous adenocarcinoma; C: Endometroid ovarian carcinoma; D: Serous adenocarcinoma; E: Fibroma; F: Fibrothecoma.

Tissue array slides (Super Bio Chips) were deparaffinized according to the manufacturer's instruction. For antigen retrieval, slides were microwaved in 10 mM citrate buffer pH 6.0 for 10 min. Endogenous peroxidase were quenched by incubation in 3% $H_2O_2$ for 5 min. In the preferred configuration the tissue sections were incubated for 1 h at room temperature with 12A2 MAb. For visualization of the bound 12A2 MAb the EnVision+System-HRP (Dako AS, Denmark) was used according to the manufacturers instructions. Slides were counterstained in hematoxylin (Dako Cytomation), mounted and analyzed by microscopy. The different ovarian cancer sections (FIG. 12 A-D) were stained for HE4a N-WFDC, while tissues from non-cancerous tissues were negative (FIG. 12 E-F).

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. An monoclonal antibody that specifically binds an epitope within the amino acid sequence of the N-WFDC domain of an HE4a polypeptide as set forth in SEQ ID NO.: 17, wherein the monoclonal antibody is produced by the hybridoma cell line 12A2, deposited with the ECACC as Patent Deposit No. 10091401, and wherein the antibody is optionally labeled with a detectable marker.

2. A kit comprising the antibody of claim 1.

3. The kit of claim 2, further comprising an antibody that specifically binds to the C-WFDC domain of an HE4a polypeptide.

4. The kit of claim 2 further comprising a second antibody that specifically binds an epitope in the N-WFDC domain of an HE4a polypeptide as set forth in SEQ ID NO: 17, wherein the second antibody recognizes an epitope distinct from the epitope recognized by the monoclonal antibody produced by the hybridoma cell line 12A2, deposited with the ECACC as Patent Deposit No. 10091401.

5. An antigen-binding fragment of the antibody of claim 1, wherein the antigen-binding fragment specifically binds the epitope recognized by the antibody produced by the hybridoma cell line 12A2, deposited with the ECACC as Patent Deposit No. 10091401.

6. A bispecific, chimeric, or humanized antibody derived from the antibody of claim 1.

* * * * *